United States Patent
Alaoui-Jamali et al.

(10) Patent No.: US 12,012,408 B2
(45) Date of Patent: Jun. 18, 2024

(54) PURINE COMPOUNDS AND METHOD FOR THE TREATMENT OF CANCER

(71) Applicant: THE ROYAL INSTITUTION FOR THE ADVANCEMENT OF LEARNING/MCGILL UNIVERSITY, Montréal (CA)

(72) Inventors: Moulay A Alaoui-Jamali, Outremont (CA); Krikor Bijian, Laval (CA); Dominik Wernic, Montréal (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 721 days.

(21) Appl. No.: 16/972,831

(22) PCT Filed: Jun. 21, 2019

(86) PCT No.: PCT/CA2019/050873
§ 371 (c)(1),
(2) Date: Dec. 7, 2020

(87) PCT Pub. No.: WO2019/241896
PCT Pub. Date: Dec. 26, 2019

(65) Prior Publication Data
US 2021/0171524 A1    Jun. 10, 2021

Related U.S. Application Data

(60) Provisional application No. 62/688,569, filed on Jun. 22, 2018.

(51) Int. Cl.
*C07D 473/16* (2006.01)
*A61P 35/00* (2006.01)

(52) U.S. Cl.
CPC ............ *C07D 473/16* (2013.01); *A61P 35/00* (2018.01)

(58) Field of Classification Search
CPC ................................. C07D 473/16; A61P 35/00
See application file for complete search history.

(56) References Cited

U.S. PATENT DOCUMENTS

| | | | |
|---|---|---|---|
| 10,711,002 B2 * | 7/2020 | Alaoui-Jamali | ..... C07D 473/16 |
| 2007/0142402 A1 | 6/2007 | Ding et al. | |

FOREIGN PATENT DOCUMENTS

| | | | |
|---|---|---|---|
| WO | 2001009134 A1 | 2/2001 | |
| WO | 2005047524 A2 | 5/2005 | |
| WO | WO 2008/135232 A1 | 11/2008 | |
| WO | WO-2009157610 A1 * | 12/2009 | ........... C12N 5/0667 |
| WO | 2010111406 A3 | 9/2010 | |
| WO | WO 2015/075598 A1 | 5/2015 | |
| WO | WO-2017052322 A1 * | 3/2017 | ............ A23L 33/10 |
| WO | WO 2017/181285 A1 | 10/2017 | |

OTHER PUBLICATIONS

Zhao; Bioorg. Med. Chem. 2012, 20, 2558-2563. https://doi.org/10.1016/j.bmc.2012.02.049 (Year: 2012).*
Cao; Clinical Cancer Research, 2004, 10, 2561-2569. https://doi.org/10.1158/1078-0432.CCR-03-0268 (Year: 2004).*
Bijian; European Journal of Medicinal Chemistry, 2012, 48, 143-152. http:/dx.doi.org/10.1016/j.ejmech.2011.12.006 (Year: 2012).*
Madhunapantula; Molecular Cancer Therapeutics, 2008, 7. 1297-1308. https://doi.org/10.1158/1535-7163.MCT-07-2267 (Year: 2008).*
Wang; Anticancer Drugs. 2011, 22, 732-740. doi: 10.1097/CAD.0b013e32834618bc. PubMed Abstract. PMID: 21562407. (Year: 2011).*
Bartalucci, N. et al. "Co-targeting the PI3K/mTOR and JAK2 signalling pathways produces synergistic activity against myeloproliferative neoplasms". J Cell Mol Med. 2013; 17. pp. 1385-1396.
Bogani, C et al. "mTOR inhibitors alone and in combination with JAK2 inhibitors effectively inhibit cells of myeloproliferative neoplasms". PLoS One 2013; 8: e54826.
Britschgi, A. et al. "JAK2/STAT5 inhibition circumvents resistance to PI3K/mTOR blockade: a rationale for cotargeting these pathways in metastatic breast cancer". Cancer Cell. 2012; 22: pp. 796-811.
Buchser, W.J. et al. "Cell-mediated autophagy promotes cancer cell survival". Cancer Res. 2012; 72: pp. 2970-2979.
Floto, R.A. et al. "Small molecule enhancers of rapamycin-induced TOR inhibition promote autophagy, reduce toxicity in Huntington's disease models and enhance killing of mycobacteria by macrophages". Autophagy. 2007; 3: pp. 620-622.

(Continued)

*Primary Examiner* — Daniel R Carcanague
(74) *Attorney, Agent, or Firm* — Christian Cawthorn; NORTON ROSE FULBRIGHT CANADA LLP

(57) ABSTRACT

The present disclosure relates to novel compound of Formula I, (I) or a pharmaceutically acceptable salt or solvate thereof; wherein Ra, Rb, Rc, Rd, ring A and ring B are as defined herein, pharmaceutical compositions containing same and methods for the treatment of cancer using same.

20 Claims, 19 Drawing Sheets
Specification includes a Sequence Listing.

(56) References Cited

OTHER PUBLICATIONS

Fulda, S. et al. "Cell death by autophagy: emerging molecular mechanisms and implications for cancer therapy". Oncogene 2015; 34. pp. 5105-5113.
Galluzzi, L. et al. "Autophagy in malignant transformation and cancer progression". EMBO J. 2015; 34: pp. 856-880.
Gewirtz, D.A. "The four faces of autophagy: implications for cancer therapy". Cancer Res 2014; 74. pp. 647-651.
Janku, F. et al. "Autophagy as a target for anticancer therapy". Nat Rev Clin Oncol. 2011; 8: pp. 528-539.
Jing, Z. et al. "Salvianolic acid B, a novel autophagy inducer, exerts antitumor activity as a single agent in colorectal cancer cells". Oncotarget. 2016; 7: pp. 61509-61519.
Kenific, C.M. et al. "Cellular and metabolic functions for autophagy in cancer cells". Trends Cell Biol. 2015; 25. pp. 37-45.
Klionsky, D.J. et al. "Guidelines for the use and interpretation of assays for monitoring autophagy". (3rd edition) Autophagy. 2016; 12: pp. 1-222.
Klionsky, D.J. et al. "Guidelines for the use and interpretation of assays for monitoring autophagy in higher eukaryotes". Autophagy. 2008; 4: pp. 151-175.
Kondo, Y. et al. "The role of autophagy in cancer development and response to therapy". Nat Rev Cancer. 2005; 5: pp. 726-734.
Kumagai, T. et al. "Histone deacetylase inhibitor, suberoylanilide hydroxamic acid (Vorinostat, SAHA) profoundly Inhibits the growth of human pancreatic cancer cells". Int J Cancer 2007; 121. pp. 656-665.
Kumar, D. V. et al. "Lead optimization of purine based orally bioavailable Mps1 (TTK) inhibitors" Bioorganic and Medicinal Chemistry Letters (2012), vol. 22, pp. 4377-4385.
Kusakabe, K. et al. "Discovery of Imidazo[1,2-b]pyridazine Derivatives: Selective and Orally Available Mps1 (TTK) Kinase Inhibitors Exhibiting Remarkable Antiproliferative Activity" J. Med. Chem. (2015), vol. 58, pp. 1760-1775.
Lebovitz, C.B. et al. "Precision autophagy: Will the next wave of selective autophagy markers and specific autophagy inhibitors feed clinical pipelines?" Autophagy. 2015; 11. pp. 1949-1952.
Lee, K.H. et al. "Targeting energy metabolic and oncogenic signaling pathways in triple-negative breast cancer by a novel adenosine monophosphate-activated protein kinase (AMPK) activator". J Biol Chem. 2011; 286: pp. 39247-39258.
Li, J. et al. "Rapamycin: one drug, many effects". Cell Metab. 2014; 19. pp. 373-379.
Liu, R. et al. "Itraconazole suppresses the growth of glioblastoma through induction of autophagy: involvement of abnormal cholesterol trafficking Autophagy". 2014; 10. pp. 1241-1255.
Mizushima, N. et al. "Methods in mammalian autophagy research". Cell 2010; 140. pp. 313-326.
Perreira, M. et al. "'Reversine' and Its 2-Substituted Adenine Derivatives as Potent and Selective A3 Adenosine Receptor Antagonists" J. Med. Chem. (2005), vol. 28, pp. 4910-4918.
Pratt, J. et al. "Induction of autophagy biomarker BNIP3 requires a JAK2/STAT3 and MT1-MMP signaling interplay in Concanavalin-A-activated U87 glioblastoma cells". Cell Signal. 2014; 26. pp. 917-924.
Rao, R. et al. "Combination of pan-histone deacetylase inhibitor and autophagy inhibitor exerts superior efficacy against triple-negative human breast cancer cells". Mol Cancer Ther. 2012; 11: pp. 973-983.
Schmelzle, T. et al. "TOR, a central controller of cell growth". Cell 2000; 103. pp. 253-262.
Shi, J. et al. "IL 10 inhibits starvation-induced autophagy in hypertrophic scar fibroblasts via cross talk between the IL10-IL 10R-STAT3 and IL 10-AKT-mTOR pathways". Cell Death Dis. 2016; 7:e2133.
Tsujimoto, Y. et al. "Another way to die: autophagic programmed cell death". Cell Death Differ. 2005; 12 Suppl 2: pp. 1528-1534.
Wang, K. et al. "Ivermectin induces PAK1-mediated cytostatic autophagy in breast cancer". Autophagy. 2016: pp. 1-2.
Yang, H. et al. "Aurora-A induces cell survival and chemoresistance by activation of Akt through a p53-dependent manner in ovarian cancer cells". Int J Cancer. 2006; 119. pp. 2304-2312.
Zhang, S. et al. "Aurora-A regulates autophagy through the Akt pathway in human prostate cancer". Cancer Biomark 2017; 19. pp. 27-34.
Zhou, L.D. et al. "RNA interference-mediated knockdown of Aurora-B alters the metastatic behavior of A549 cells via modulation of the phosphoinositide 3-kinase/Akt signaling pathway". Oncol Lett. 2014; 8. pp. 2063-2068.
Zhu, L.B. et al. "Knockdown of Aurora-B inhibits osteosarcoma cell invasion and migration via modulating PI3K/Akt/NF-kappaB signaling pathway". Int J Clin Exp Pathol. 2014; 7. pp. 3984-3991.
Zou, Z. et al. "Aurora kinase A inhibition-induced autophagy triggers drug resistance in breast cancer cells". Autophagy 2012; 8. pp. 1798-1810.

* cited by examiner

FIG. S1.

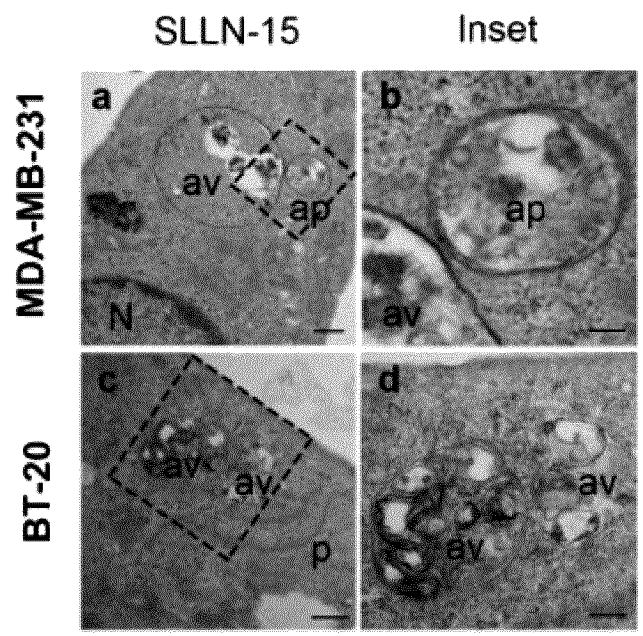
FIG. 2C
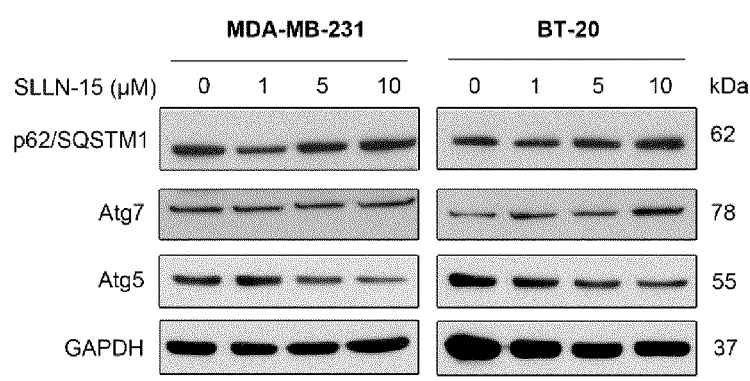
FIG. S2

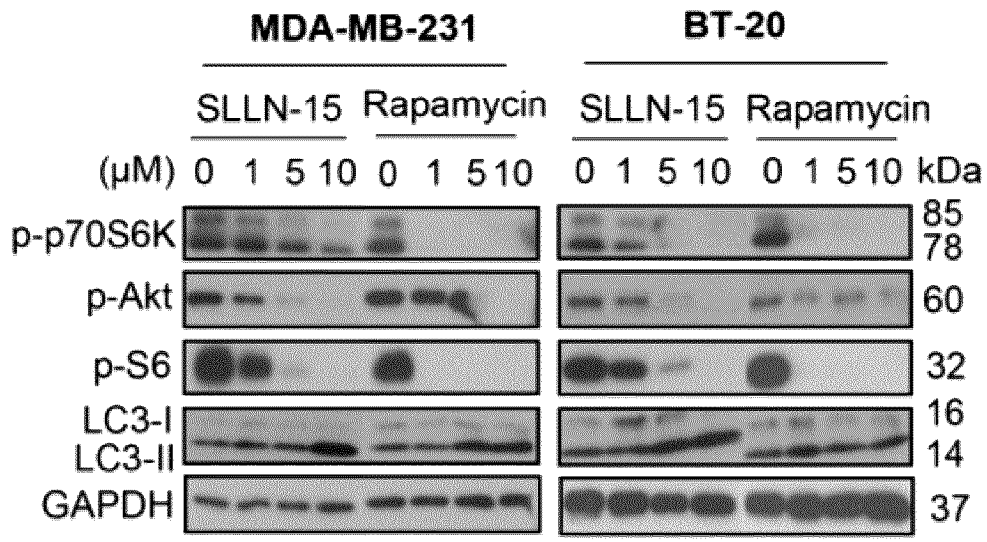
FIG. 6E
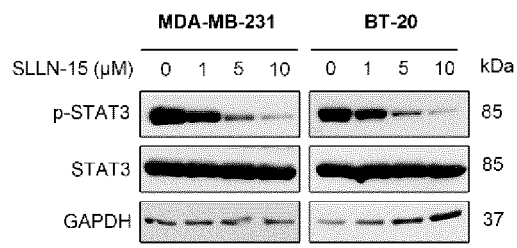
FIG. S3

PURINE COMPOUNDS AND METHOD FOR THE TREATMENT OF CANCER

CROSS REFERENCE TO RELATED APPLICATIONS

The present application is the 371 national phase entry of PCT/CA2019/050873 filed Jun. 21, 2019, the content of which is hereby incorporated in its entirety. The present application also claims priority from US provisional patent application Ser. No. 62/688,569, filed Jun. 22, 2018 and entitled "PURINE COMPOUNDS AND METHOD FOR THE TREATMENT OF CANCER", the disclosure of which is hereby incorporated by reference in its entirety.

FIELD OF THE DISCLOSURE

The present disclosure relates to novel compounds, pharmaceutical compositions containing same and methods for the treatment of cancer using same.

BACKGROUND OF THE DISCLOSURE

A broad group of diseases involving unregulated cell growth is known as cancer or as malignant neoplasia. In cancer, cells divide and grow uncontrollably, causing the cells to form lumps or tumors. The cancer may also spread to more distant parts of the body through the lymphatic system or bloodstream.

Mortality from cancer is primarily attributed to the dissemination of primary tumor cells to distant organs, attributed to a subset of genetically selected cancer cell variants with intrinsic invasive capacity.

An example of cancer is breast cancer which is a heterogeneous disease with diverse histologic and molecular subtypes, each having distinct clinical implications. Among the various subtypes, triple-negative breast cancer (TNBC) which represents approximately 15% of breast carcinomas often manifests with an aggressive behaviour and high rates of recurrence. TNBC is biologically distinct from the other breast cancer subtypes due to lack of expression of estrogen receptor (ER), progesterone receptor (PR), as well as overexpression/amplification of human epidermal growth factor receptor type 2 (HER2). Currently, non-selective chemotherapy remains the cornerstone therapeutic for TNBC but with limited benefits to patients.

Macroautophagy (hereafter referred to as autophagy) is an evolutionarily conserved catabolic pathway involved in the degradation of damaged or dysfunctional intracellular cellular components delivered by double-membrane autophagosomes to lysosomes (Kondo Y, et al. *The role of autophagy in cancer development and response to therapy* Nat Rev Cancer 2005; 5:726-34). Autophagy is regulated by various signaling pathways, including AMP-activated protein kinase (AMPK) and mammalian target of rapamycin (mTOR) signalling (Galluzzi L et al. *Autophagy in malignant transformation and cancer progression* EMBO J 2015; 34:856-80). The role of autophagy in the regulation of tumorigenesis remains debated. Depending on tumor types and treatment strategies, autophagy fulfills a dual role, having pro-survival or pro-death properties (Janku F et al. *Autophagy as a target for anticancer therapy* Nat Rev Clin Oncol 2011; 8:528-39). On one hand, autophagy can be activated as a cytoprotective mechanism in response to anticancer agents to mediate drug resistance; in this case inhibition of autophagy can achieve therapeutic advantage by sensitizing cells to anticancer agents (Buchser W J et al. *Cell-mediated autophagy promotes cancer cell survival* Cancer Res 2012; 72:2970-9). On the other hand, autophagy may also function as a pro-death signal to induce autophagic-mediated cell killing (type II programmed cell death), which is a distinct form of caspase-independent cell death in contrast to apoptosis (type I programmed cell death) (Tsujimoto Y et al *Another way to die: autophagic programmed cell death* Cell Death Differ 2005; 12 Suppl 2:1528-34).

Both autophagy inducers and inhibitors have been exploited for therapeutic applications. For instance, autophagy inhibitors such as chloroquine (CQ) or hydrochloroquine (HCQ) have shown promising results in TNBC preclinical models, especially in combination with conventional chemotherapy (Lee K H et al. *Targeting energy metabolic and oncogenic signaling pathways in triple-negative breast cancer by a novel adenosine monophosphate-activated protein kinase (AMPK) activator* J Biol Chem 2011; 286:39247-58; Rao R et al. *Combination of pan-histone deacetylase inhibitor and autophagy inhibitor exerts superior efficacy against triple-negative human breast cancer cells* Mol Cancer Ther 2012; 11:973-83), and are undergoing clinical trials (clinicaltrials.gov). In contrast to autophagy inhibitors, therapeutic utility was also reported for autophagy inducers; e.g. Ivermectin, salvianolic acid B or rapamycin, autophagy inducers that have been reported to inhibit cancer cell growth in part by enhancing anti-tumor immunity (Wang K et al. *Ivermectin induces PAK1-mediated cytostatic autophagy in breast cancer* Autophagy 2016:1-2; Jing Z et al. *Salvianolic acid B, a novel autophagy inducer, exerts antitumor activity as a single agent in colorectal cancer cells* Oncotarget 2016; 7:61509-19). Therefore, these findings support the potential of utilizing autophagy enhancers as a novel therapeutic strategy in cancer.

Considering the vast functional nature of autophagy, the potential utility of active molecules extend beyond cancer, as autophagy upregulation has been documented in numerous chronic conditions, such as preventing the accumulation of aggregate-prone cytosolic proteins in neurodegenerative diseases and promoting engulfment/degradation of certain bacterial (tuberculosis and *streptococcus*) and viral infections (herpes simplex) (Floto R A et al. *Small molecule enhancers of rapamycin-induced TOR inhibition promote autophagy, reduce toxicity in Huntington's disease models and enhance killing of mycobacteria by macrophages* Autophagy 2007; 3:620-2).

SUMMARY OF THE DISCLOSURE

In one aspect, there is provided a compound of formula

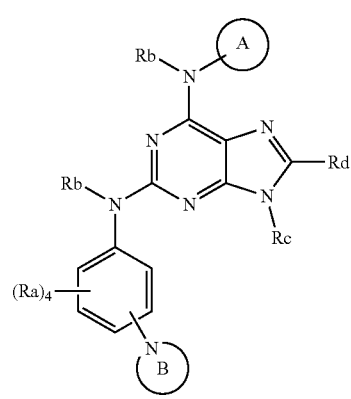

or a pharmaceutically acceptable salt or solvate thereof;

wherein
- Ra is independently H, a straight or branched alkyl substituted or not with a halogen, lower cycloalkyl, straight or branched alkoxy substituted or not with a halogen, heteroaryl or halogen,
- Rb is H or a lower straight or branched alkyl,
- Rc is H or a lower straight or branched alkyl substituted or not with a halogen,
- Rd is H, halogen or an alkyl of 1 to 6 carbon atoms,
- ring A is an optionally substituted saturated ring attached by a carbon atom of said ring to the nitrogen atom at the C-6 position of the purine core, said ring is comprising 5 to 7 members, and is optionally comprising one or two selenium atoms as ring constituting atoms, and wherein two selenium atoms are adjacent or non-adjacent, or ring A is an optionally substituted 5 to 7 members bridged bicycloalkyl, and
- ring B is an optionally substituted saturated ring attached by a nitrogen atom of said ring to a carbon atom of the phenylene residue, and wherein said ring is comprising 5 to 7 members, and is optionally comprising one oxygen atom or one or two selenium atoms as ring constituting atoms, and wherein two selenium atoms are adjacent or non-adjacent.

In another aspect of the disclosure, there is provided a pharmaceutical composition comprising a compound as defined herein or a pharmaceutically acceptable salt or solvate thereof, and one or more pharmaceutically acceptable carrier and/or excipient.

In one aspect, there is provided a method, composition, use or combination for selectively co-modulating and/or co-inhibiting the function of Aurora A and Jak2 kinases.

In one aspect, there is provided a method, composition, use or combination for reducing or inhibiting metastasis of metastatic cells, comprising administering to a patient in need thereof a therapeutically effective amount of a compound or a pharmaceutically acceptable salt thereof, as defined herein.

In one aspect, there is provided a method, composition, use or combination for treating a cancer, comprising administering to a patient in need thereof a therapeutically effective amount of a compound or a pharmaceutically acceptable salt thereof as defined herein.

In one aspect, there is provided a method, composition or use for treating cancer comprising administering to a patient in need thereof a compound as defined herein and an additional anticancer drug.

In one aspect, there is provided a method, composition, use or combination for reducing or stopping the proliferation of cancer cells comprising administering to a patient in need thereof a therapeutically effective amount of a compound or a pharmaceutically acceptable salt thereof as defined herein.

In one aspect, there is provided a method, composition, use or combination for reducing or stopping the proliferation of cancer cells comprising administering to a patient in need thereof a therapeutically effective amount of a compound or a pharmaceutically acceptable salt thereof as defined herein and an additional drug useful for reducing or stopping the proliferation of cancer cells.

BRIEF DESCRIPTION OF THE DRAWINGS

FIG. 2C represents the transmission electron microscopy of SLLN-15 treated MDA-MB-231 and BT-20 cells. N is the nucleus, av is autophagic vacuoles, ap is autophagosome and p is phagophore.

FIG. 6E is a western blot of MDA-MB-231 and BT-20 cells treated with either DMSO, rapamycin or SLLN-15, immunoblotted with antibodies against p-T421/S424-p70S6K, p-S473-Akt, p-S240/244-S6, LC3B and GAPDH.

Figure 1A:
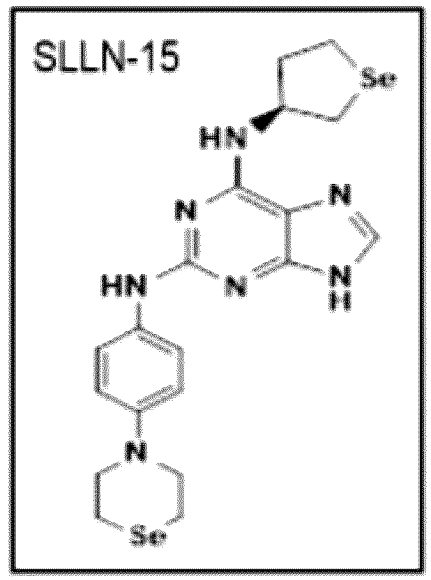
FIG. 1A is the chemical structure of a representative compound.

FIG. S1 represents the cell morphological changes of MDA-MB-231 and BT-20 upon SLLN-15 treatment as visualized by light microscopy.

FIG. S2 is a western blot of MDA-MB-231 and BT-20 cells treated with either DMSO or SLLN-15, immunoblotted with antibodies against p62/SQSTM1, Atg7, Atg5 and GAPDH.

FIG. S3A represents the SelectScreen kinase profiling (Invitrogen) results obtained against a panel of kinases for SLLN-15 at 100 nM.

FIG. S3B is a western blot of MDA-MB-231 and BT-20 cells treated with either DMSO or SLLN-15, immunoblotted with anti-p-Y705 STAT3, anti-STAT3 and anti-GAPDH antibodies.

DESCRIPTION OF THE EMBODIMENTS

The present disclosure relates to novel compounds that have the ability to selectively co-modulate and/or co-inhibit the function of selected kinases simultaneously, namely Aurora A and Jak2 kinases, which are unregulated in many cancer cell variants enriched in stem cell markers. Aurora A and Jak2 kinases have been reported to be directly involved in pathways controlling cell differentiation programs, metastasis signaling, as well as epithelial and mesenchymal transition (EMT) and CSC programming and their overexpression was reported to predict decreased metastasis-free survival.

Aurora A is a key serine/threonine kinase commonly overexpressed in various human cancers and considered to act as an oncoprotein that regulates cell growth differentiation and cell invasion. Its overexpression predicts poor prognosis. Several preclinical studies have shown that inhibition of Aurora A by pharmacological approaches or RNA interference effectively blocks mitosis and other key oncogenic signals.

Jak2 is a cytoplasmic protein tyrosine kinase required for signaling in particular from receptors that lack intrinsic kinase activity. Signaling through Jak2 has a broad function in cytokine metabolism, inflammatory response, and is generally seen as prosurvival and as a proliferative marker in most cancer types. Moreover, activating mutations of Jak2 have been shown to drive progression of leukemic and myeloproliferative neoplasms.

Inhibitors that co-target these kinases simultaneously through distinct mechanisms have the potential to inhibit tumor growth and progression with increased potency/efficacy, evading drug-resistance and providing an alternative therapeutic strategy for incurable cancers.

In accordance with any aspect on the compound, method, use, composition of combination herein, the compounds defined herein (including in formula I, II or II) have at least one of ring A and ring B comprising one or two ring constituting selenium atom.

In accordance with one embodiment, there is provided a compound of formula

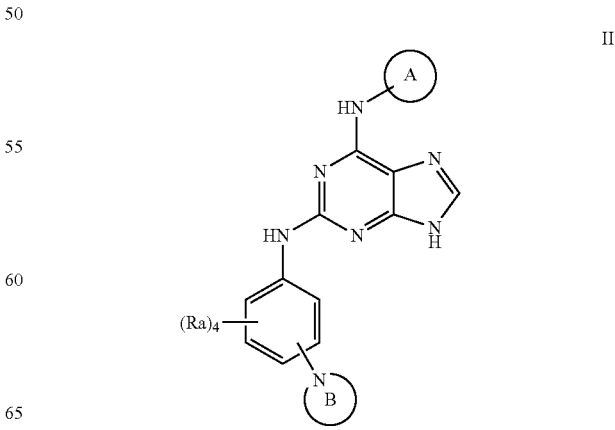

II or a pharmaceutically acceptable salt or solvate thereof; wherein Ra, ring A and ring B are as defined herein, provided at least one of ring A and ring B is comprising one or two ring constituting selenium atom.

In accordance with a further embodiment, there is provided a compound of formula

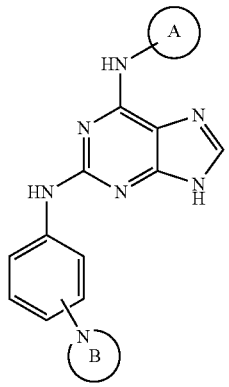

III or a pharmaceutically acceptable salt or solvate thereof, wherein ring A and ring B are as defined herein.

As used herein, (Ra)$_4$ refers to four (4) Ra substituents being present on the phenylene ring, that is one on each available carbon atom of that ring.

In one embodiment, each Ra is independently H, a straight or branched alkyl, lower cycloalkyl, straight or branched alkoxy, heteroaryl or halogen.

In one embodiment, each Ra is independently H, a lower straight or branched alkyl, lower cycloalkyl, lower straight or branched alkoxy, heteroaryl of 5-6 members or halogen.

In one embodiment, each Ra is independently H, a straight alkyl of 1-3 carbon atoms, or branched alkyl of 3 carbon atoms, straight alkoxy of 1-3 carbon atoms or branched alkoxy of 3 carbon atoms, cycloalkyl of 3 carbon atoms, heteroaryl of 5-6 members or fluoride atom.

In one embodiment, each Ra is independently H, a straight alkyl or fluoroalkyl of 1-3 carbon atoms; branched alkyl or fluoroalkyl of 3 carbon atoms; straight alkoxy or fluoroalkoxy of 1-3 carbon atoms; branched alkoxy or fluoroalkoxy of 3 carbon atoms, cycloalkyl of 3 carbon atoms, heteroaryl of 5-6 members or fluoride atom.

In one embodiment, each Ra is independently H, methyl, ethyl, n-propyl, isopropyl, n-butyl, sec-butyl, ter-butyl, trifluoromethyl, trifluoromethoxy, methoxy, cyclopropyl, cyclobutyl, cyclopentyl cyclohexyl, heteroaryl of 5-6 members comprising at least one heteroatom selected from oxygen (O), and nitrogen (N); or fluoride atom.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom.

In one embodiment, Rb is H or a lower straight or branched alkyl. In a further embodiment, Rb is H or methyl, ethyl, n-propyl, isopropyl. In a further embodiment, Rb is H.

In one embodiment, Rc is H or a lower straight or branched alkyl. In a further embodiment, Rc is H or methyl, ethyl, n-propyl, isopropyl or trifloromethyl. In a further embodiment, Rc is H.

In one embodiment, Rd is H, halogen, alkyl of 1 to 6 carbon atoms.

In one embodiment, Rd is H, halogen, C1-3alkyl. In a further embodiment, Rd is H, F, Cl, Br, methyl, ethyl, propyl, isopropyl. In a further embodiment, Rd is H, Cl or methyl.

In a further embodiment, Rd is H.

In one embodiment, ring A is an optionally substituted saturated ring attached by a carbon atom of said ring to the nitrogen atom at the C-6 position of the purine core, said ring is comprising 5 to 7 members, and is optionally comprising one or two selenium atoms as ring constituting atoms, and wherein two selenium atoms are adjacent or non-adjacent.

In one embodiment, ring A is an optionally substituted, saturated 5 to 7 members cycloalkyl or an optionally substituted 5 to 7 members bridged bicycloalkyl.

In one embodiment, ring A is an optionally substituted, saturated 5 to 7 members cycloalkyl.

In one embodiment, ring A is an optionally substituted cyclopentyl or cyclohexyl.

In one embodiment, ring A is

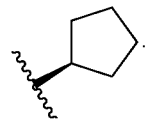

In one embodiment, ring A is

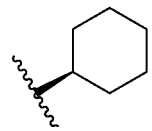

In one embodiment, ring A is an optionally substituted saturated bridged bicycloalkyl.

In one embodiment, ring A is an optionally substituted bicyclo[2,2,1] heptyl or bicyclo[3,1,1] heptyl.

In one embodiment, ring A is

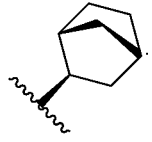

In one embodiment, ring A is

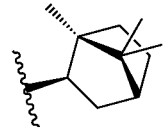

In one embodiment, ring A is an optionally substituted, saturated ring of 5 to 7 members, comprising one or two ring constituting selenium atom.

In one embodiment, ring A is a tetrahydroselenophene, a selenane, a diselenolane or a diselenane.

In further embodiments:

A tetrahydroselenophene may be tetrahydroselenophene-2yl or -3yl, preferably a tetrahy droselenophene-3yl.

A selenane may be selenane-2yl, -3yl or 4-yl, preferably a selenane-3yl.

A diselenolane may be a 1,2-diselenolane or a 1,3-diselenolane, preferably a 1,2-diselenolane-3yl.

A diselenane may be a 1,2-diselenane, a 1,3-diselenane or a 1,4-diselenane, preferably a 1,2-diselenane-4yl.

In one embodiment, ring A is

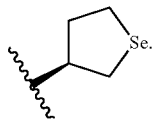

In one embodiment, ring A is

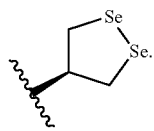

In one embodiment, ring A is

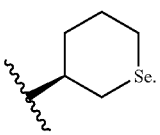

In one embodiment, ring A is

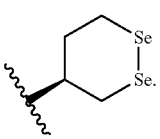

For greater clarity, exemplary structures of tetrahydroselenophene, selenane, diselenolane and diselenane rings of ring A are as follow:

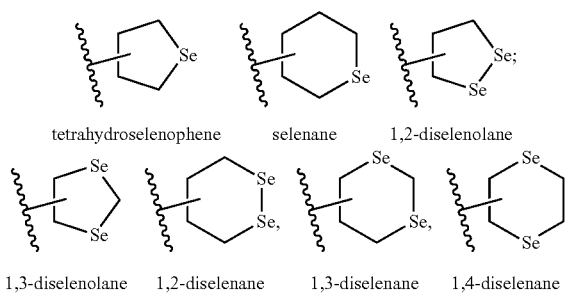

tetrahydroselenophene    selenane    1,2-diselenolane 1,3-diselenolane    1,2-diselenane    1,3-diselenane    1,4-diselenane In one embodiment, ring B is an optionally substituted saturated ring attached by a nitrogen atom of said ring to a carbon atom of the phenylene residue, and wherein said ring is comprising 5 to 7 members, and is optionally comprising one oxygen atom or one or two selenium atoms as ring constituting atoms, and wherein two selenium atoms are adjacent or non-adjacent.

In one embodiment, ring B is an optionally substituted saturated ring attached by a nitrogen atom of said ring to a carbon atom of the phenylene residue, and wherein said ring is comprising 5 to 7 members, and is comprising one oxygen atom or one or two selenium atoms as ring constituting atoms, and wherein two selenium atoms are adjacent or non-adjacent.

In one embodiment, ring B is an optionally substituted morpholinyl group.

In one embodiment, ring B is an optionally substituted saturated ring attached by a nitrogen atom of said ring to a carbon atom of the phenylene residue, and wherein said ring is comprising 6 members, and is comprising one selenium atom as ring constituting atoms.

In one embodiment, ring B is an optionally substituted saturated ring attached by a nitrogen atom of said ring to a carbon atom of the phenylene residue, and wherein said ring is comprising 7 members, and is comprising two selenium atoms as ring constituting atoms, and wherein said selenium atoms are adjacent.

In one embodiment, ring B is an optionally substituted saturated ring attached by a nitrogen atom of said ring to a carbon atom of the phenylene residue, and wherein said ring is comprising 6 or 7 members, and is comprising one or two selenium atoms as ring constituting atoms, and wherein two selenium atoms are adjacent or non-adjacent.

In one embodiment, ring B is a morpholinyl, a selenomorpholin-4yl of formula

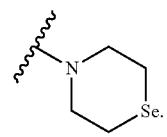

or a 1,2-diselenazepan-5-yl of formula

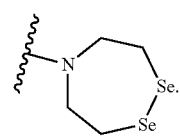

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; R1 is an optionally substituted selenium-containing heterocycle of 5 or 6 members; Rd is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; R1 is an optionally substituted bridged bicycloalkyl of 7 or 8 carbon atoms; Rd is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; R1 is an optionally substituted bicyclo[2,2,1] heptyl or bicyclo[3,1,1] heptyl; Rd is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; and Rd is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; and Rd is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H, and Rd is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; Rd is H.

In one embodiment, each Ra is H; Rb is H; Rc is H; Rd is H.

In one embodiment, each Ra is independently H, a straight or branched alkyl, lower cycloalkyl, straight or branched alkoxy, heteroaryl or halogen; each Rb is H or a lower straight or branched alkyl; Rc is H or a lower straight or branched alkyl; Rd is H, halogen, alkyl; ring A is an optionally substituted, saturated 5 to 7 members cycloalkyl or an optionally substituted 5 to 7 members bridged bicycloalkyl or an optionally substituted, saturated ring of 5 to 7 members, comprising one or two ring constituting selenium atom and ring B is an optionally substituted saturated ring attached by a nitrogen atom of said ring to a carbon atom of the phenylene residue, and wherein said ring is comprising 5 to 7 members, and is optionally comprising one or two selenium atoms as ring constituting atoms, and wherein two selenium atoms are adjacent or non-adjacent.

In one embodiment, each Ra is independently H, a straight alkyl of 1-3 carbon atoms, or branched alkyl of 3 carbon atoms, straight alkoxy of 1-3 carbon atoms or branched alkoxy of 3 carbon atoms, cycloalkyl of 3 carbon atoms, heteroaryl of 5-6 members or fluoride atom; Rb is H or methyl, ethyl, n-propyl, isopropyl; Rc is H or methyl, ethyl, n-propyl, isopropyl or trifloromethyl; Rd is H, halogen, alkyl of 1 to 6 carbon atoms, ring A is an optionally substituted, saturated 5 to 7 members cycloalkyl or an optionally substituted 5 to 7 members bridged bicycloalkyl and ring B is an optionally substituted saturated ring attached by a nitrogen atom of said ring to a carbon atom of the phenylene residue, and wherein said ring is comprising 5 to 7 members, and is comprising one or two selenium atoms as ring constituting atoms, and wherein two selenium atoms are adjacent or non-adjacent.

In one embodiment, each Ra is independently H, a straight alkyl of 1-3 carbon atoms, or branched alkyl of 3 carbon atoms, straight alkoxy of 1-3 carbon atoms or branched alkoxy of 3 carbon atoms, cycloalkyl of 3 carbon atoms, heteroaryl of 5-6 members or fluoride atom; Rb is H or methyl, ethyl, n-propyl, isopropyl; Rc is H or methyl, ethyl, n-propyl, isopropyl or trifloromethyl; Rd is H, halogen, alkyl of 1 to 6 carbon atoms, ring A is an optionally substituted, saturated ring of 5 to 7 members, comprising one or two ring constituting selenium atom and ring B is an optionally substituted saturated ring attached by a nitrogen atom of said ring to a carbon atom of the phenylene residue, and wherein said ring is comprising 5 to 7 members.

In one embodiment, each Ra is independently H, a straight alkyl of 1-3 carbon atoms, or branched alkyl of 3 carbon atoms, straight alkoxy of 1-3 carbon atoms or branched alkoxy of 3 carbon atoms, cycloalkyl of 3 carbon atoms, heteroaryl of 5-6 members or fluoride atom; Rb is H or methyl, ethyl, n-propyl, isopropyl; Rc is H or methyl, ethyl, n-propyl, isopropyl or trifloromethyl; Rd is H, halogen, alkyl of 1 to 6 carbon atoms, ring A or an optionally substituted, saturated ring of 5 to 7 members, comprising one or two ring constituting selenium atom and ring B is an optionally substituted saturated ring attached by a nitrogen atom of said ring to a carbon atom of the phenylene residue, and wherein said ring is comprising 5 to 7 members, and is comprising one or two selenium atoms as ring constituting atoms, and wherein two selenium atoms are adjacent or non-adjacent.

In one embodiment, each Ra is independently H, methyl, ethyl, n-propyl, isopropyl, n-butyl, sec-butyl, ter-butyl, trifluoromethyl, trifluoromethoxy, methoxy, cyclopropyl, cyclobutyl, cyclopentyl cyclohexyl, heteroaryl of 5-6 members comprising at least one heteroatom selected from oxygen (O), and nitrogen (N); or fluoride atom; Rb is H; Rc is H; Rd is H, Cl, methyl, ring A is an optionally substituted, saturated ring of 5 to 7 members, comprising one or two ring constituting selenium atom and ring B is an optionally substituted saturated ring attached by a nitrogen atom of said ring to a carbon atom of the phenylene residue, and wherein said ring B is comprising 5 to 7 members, and is optionally comprising one oxygen atom or one or two selenium atoms as ring constituting atoms, and wherein two selenium atoms are adjacent or non-adjacent.

In one embodiment, each Ra is independently H, methyl, ethyl, n-propyl, isopropyl, n-butyl, sec-butyl, ter-butyl, trifluoromethyl, trifluoromethoxy, methoxy, cyclopropyl, cyclobutyl, cyclopentyl cyclohexyl, heteroaryl of 5-6 members comprising at least one heteroatom selected from oxygen (O), and nitrogen (N); or fluoride atom; Rb is H; Rc is H; Rd is H, Cl, methyl, ring A is a tetrahydroselenophene, a selenane, a diselenolane or a diselenane, or ring A is saturated 5 to 7 members cycloalkyl or saturated bridged bicycloalkyl and ring B is an optionally substituted saturated ring attached by a nitrogen atom of said ring to a carbon atom of the phenylene residue, and wherein said ring B is comprising 6 or 7 members, and is comprising one or two selenium atoms as ring constituting atoms, and wherein two selenium atoms are adjacent or non-adjacent.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; Rd is H, ring A is a tetrahydroselenophene, a selenane, a diselenolane or a diselenane and ring B is an optionally substituted saturated ring attached by a nitrogen atom of said ring to a carbon atom of the phenylene residue, and wherein said ring is comprising 5 to 7 members, and is comprising one oxygen atom or one or two selenium atoms as ring constituting atoms, and wherein two selenium atoms are adjacent or non-adjacent.

In one embodiment, each Ra is H; Rb is H; Rc is H; Rd is H, ring A is an optionally substituted, saturated 5 to 7 members cycloalkyl or an optionally substituted 5 to 7 members bridged bicycloalkyl and ring B is an optionally substituted saturated ring attached by a nitrogen atom of said ring to a carbon atom of the phenylene residue, and wherein said ring is comprising 5 to 7 members, and is comprising one or two selenium atoms as ring constituting atoms, and wherein two selenium atoms are adjacent or non-adjacent.

In one embodiment, each Ra is H; Rb is H; Rc is H; Rd is H, ring A is an optionally substituted, saturated ring of 5 to 7 members, comprising one or two ring constituting selenium atom and ring B is an optionally substituted saturated ring attached by a nitrogen atom of said ring to a carbon atom of the phenylene residue, and wherein said ring is comprising 5 to 7 members.

In one embodiment, each Ra is H; Rb is H; Rc is H; Rd is H, ring A or an optionally substituted, saturated ring of 5 to 7 members, comprising one or two ring constituting selenium atom and ring B is an optionally substituted saturated ring attached by a nitrogen atom of said ring to a carbon atom of the phenylene residue, and wherein said ring is comprising 5 to 7 members, and is comprising one or two selenium atoms as ring constituting atoms, and wherein two selenium atoms are adjacent or non-adjacent.

In one embodiment, ring A is an optionally substituted, saturated 5 to 7 members cycloalkyl or an optionally substituted 5 to 7 members bridged bicycloalkyl or an optionally substituted, saturated ring of 5 to 7 members, comprising one or two ring constituting selenium atom and ring B is an optionally substituted saturated ring attached by a nitrogen atom of said ring to a carbon atom of the phenylene residue, and wherein said ring B is comprising 5 to 7 members, and is optionally comprising one or two selenium atoms as ring constituting atoms, and wherein two selenium atoms are adjacent or non-adjacent.

In one embodiment, ring A is a tetrahydroselenophene, a selenane, a diselenolane or a diselenane, or ring A is saturated 5 to 7 members cycloalkyl or saturated bridged bicycloalkyl and ring B is an optionally substituted saturated ring attached by a nitrogen atom of said ring to a carbon atom of the phenylene residue, and wherein said ring B is comprising 6 or 7 members, and is comprising one or two selenium atoms as ring constituting atoms, and wherein two selenium atoms are adjacent or non-adjacent.

In one embodiment, ring A is

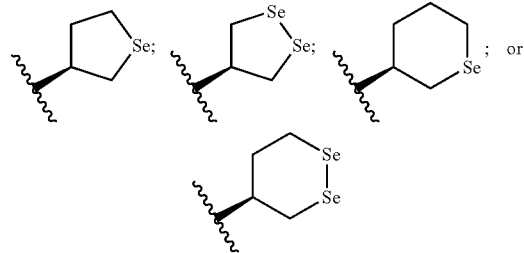

or ring A is

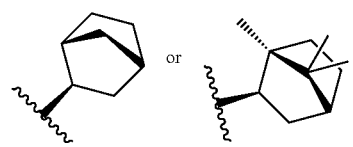

and ring B is a morpholinyl, a selenomorpholin-4yl of formula

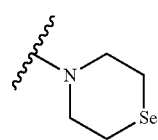 [SMILES: *N1CC[Se]CC1]

or a 1,2-diselenazepan-5-yl of formula

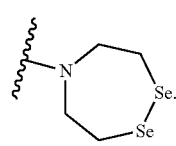

In one embodiment, exemplary compounds of the disclosure include:

Compound 1 (SLLN 10)

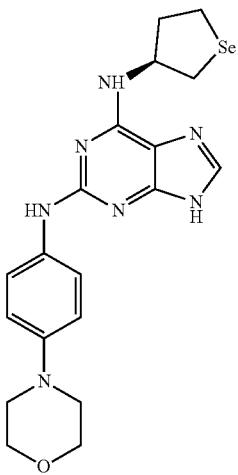

Compound 2 (SLLN 13)

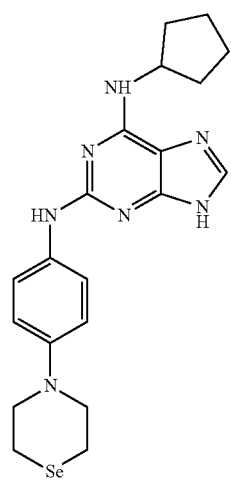

Compound 3 (SLLN 15)

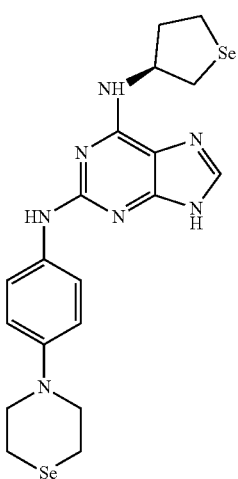

-continued
Compound 4 (SLLN 17)
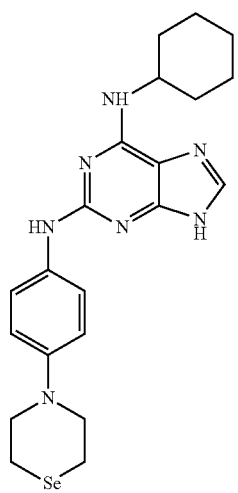
Compound 5 (SLLN 16)
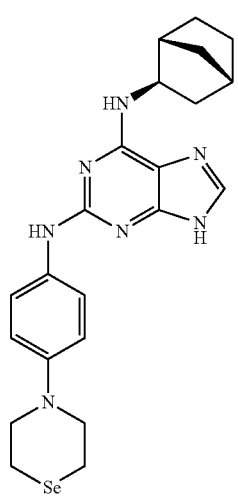
Compound 6 (SLLN 20)
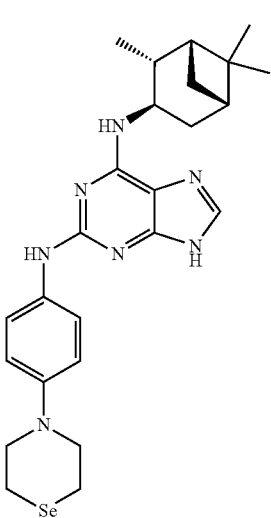
-continued
Compound 7 (SLLN 21)
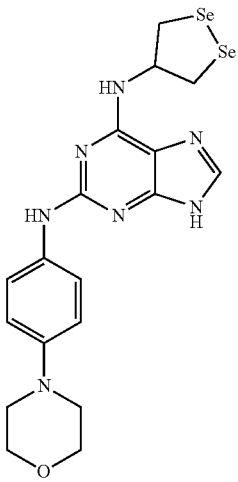
Compound 8 (SLLN 24)
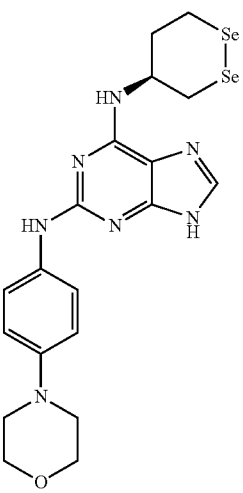
Compound 9 (SLLN 25)
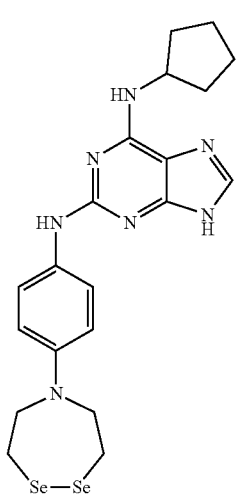

Compound 10 (SLLN 32)

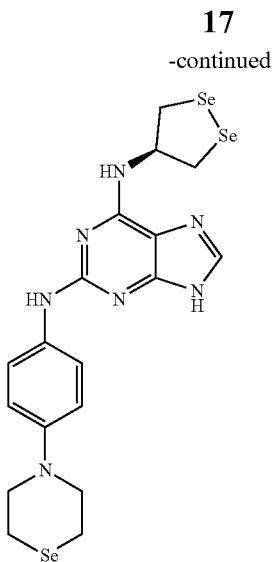

Compound 11 (SLLN 33)

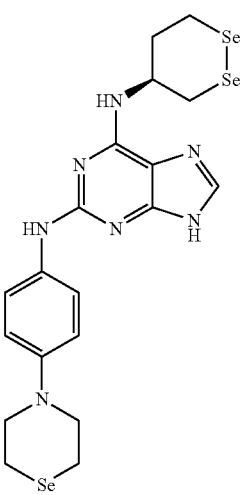

Compound 12 (SLLN 34)

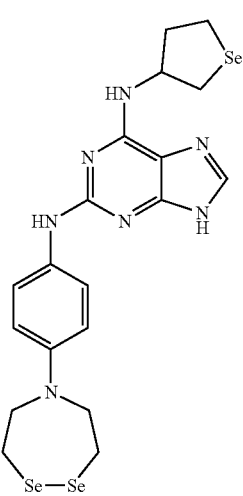

Compound 13 (SLLN 35)

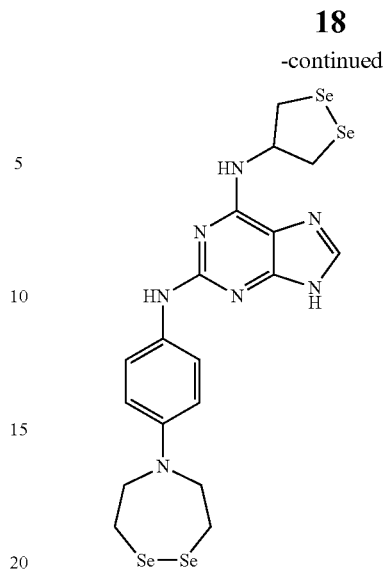

Compound 14 (SLLN 36)

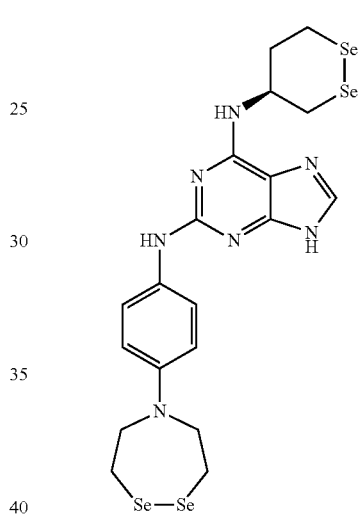

The term "alkyl", as used herein, is understood as referring to a saturated, monovalent unbranched or branched hydrocarbon chain. Examples of alkyl groups include, but are not limited to, C1-10 alkyl groups, provided that branched alkyls comprise at least 3 carbon atoms, such as C3-10. Lower straight alkyl may have 1 to 6 or preferably 1 to 3 carbon atoms; whereas branched lower alkyl comprise C3-6. Examples of alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, nonyl and decyl. The term "alkyl" is also meant to include alkyls in which one or more hydrogen atom is replaced by a halogen, ie. an haloalkyl including fluoroalkyls of all alkyls defined above: straight or branched fluoroalkyls and straight or branched lower fluoroalkyls, such as trifluoromethyl, difluoromethyl, fluoromethyl, trichloromethyl, dichloromethyl, chloromethyl, trifluoroethyl, difluoroethyl, fluoroethyl.

The terms "alkoxy," represent an alkyl, alkenyl or alkynyl moiety, respectively, which is covalently bonded to the adjacent atom through an oxygen atom.

The term "aryl" represents carbocyclic moiety containing at least one benzenoid-type ring (i.e., may be monocyclic or polycyclic). Examples include but are not limited to phenyl, tolyl, dimethylphenyl, aminophenyl, anilinyl, naphthyl, anthryl, phenanthryl or biphenyl. Preferably, the aryl comprises 6 to 10 or more preferably 6 carbon atoms.

The term "cycloalkyl" represents optionally substituted cyclic hydrocarbon moiety having 3 to 10 carbon atoms. Examples of "cycloalkyl" groups include but are not limited to cyclopropyl, cyclobutyl, cyclopentyl, and cyclohexyl. Lower cycloalkyls comprise 3 to 6, or alternatively any of 3, 4, 5 or 6 carbon atoms. This term includes without limitation, for example, cyclopropyl, cyclobutyl, cyclopentyl and cyclohexyl.

The term "heteroaryl" represents a 5 to 11 membered aromatic cyclic moiety wherein said cyclic moiety is comprising at least one heteroatom selected from oxygen (O), sulfur (S) or nitrogen (N). Heteroaryls may be monocyclic or polycyclic rings. Heteroaryls may be 5 to 6 membered monocyclic ring or 5 membered monocyclic ring or 6 membered monocyclic ring. membered monocyclic ring may be 7 to 12 membered bicyclic ring or 9 to 10 membered bicyclic ring. When heteroaryl is a polycyclic ring, the rings comprise at least one ring comprising the heteroatom and the other rings may be cycloalkyl, aryl or heterocycle and the point of attachment may be on any available atom. This term includes without limitation, for example, furyl, thienyl, pyrrolyl, imidazolyl, oxazolyl, thiazolyl, triazolyl, tetrazolyl, pyridyl, pyrazinyl, pyrimidinyl, pyridazinyl, quinolinyl, isoquinolinyl, indolyl.

The term "heterocycle" represents a 3 to 11 membered saturated, partially saturated (i.e. comprising one or more double bonds provided that it is not aromatic) cyclic moiety wherein said cyclic moiety is comprising at least one heteroatom selected from oxygen (O), sulfur (S) or nitrogen (N). Heterocycles may be monocyclic or polycyclic rings. Heterocycles may be 3 to 6 membered monocyclic ring or 5 to 6 membered monocyclic ring. When heterocycle is a polycyclic ring, the rings comprise at least one ring comprising the heteroatom and the other rings may be cycloalkyl, aryl or heterocycle and the point of attachment may be on any available atom. This term includes without limitation, for example, aziridinyl, oxiranyl, thiiranyl, azirinyl, oxirenyl, thiirenyl, azetidinyl, oxetanyl, oxetyl, pyrrolidinyl, oxolanyl, thiolanyl, piperidinyl, oxanyl, thianyl, azepanyl, oxepanyl, morpholinyl, piperazinyl, homopiperazinyl.

The term "selenium-containing heterocycle" represents a 3 to 10 membered saturated cyclic moiety wherein said cyclic moiety is comprising at least one selenium (Se), preferably one Se, atom in cyclic ring. Heterocycles may be monocyclic or polycyclic rings. Heterocycles may be 3 to 7 membered monocyclic ring, preferably 5 to 6 membered monocyclic ring.

As used herein, the expression "alkyl", "alkoxy", "aryl", "cycloalkyl", "heteroaryl", "heterocycle", "alkoxy," "alkenyloxy," "alkynyloxy", selenium-containing heterocycle and bridged bicycloalkyl, bicyclo[3,1,1] heptyl or bicyclo[2,2,1] heptyl (including lower alkyl and lower cycloalkyl) are all independently optionally substituted by one or more substituents.

The term "optionally substituted", "optionally substituent" or "substituent" represents at each occurance and independently, one or more halogen, amino, amidino, amido, azido, cyano, guanido, hydroxyl, nitro, nitroso, urea, OS(O)2Rm (wherein Rm is selected from C1-6alkyl, C6-10aryl or 3-10 membered heterocycle), OS(O)2ORn (wherein Rn is selected from H, C1-6alkyl, C6-10aryl or 3-10 membered heterocycle), S(O)2ORp (wherein Rp is selected from H, C1-6alkyl, C6-10aryl and 3-10 membered heterocycle), S(O)0-2Rq (wherein Rq is selected from H, C1-6alkyl, C6-10aryl or 3-10 membered heterocycle), OP(O)ORsORt, P(O)ORsORt (wherein Rs and Rt are each independently selected from H or C1-6alkyl), C1-6alkyl, C6-10aryl-C1-6alkyl, C6-10aryl, C1-6alkoxy, C6-10aryl-C1-6alkyloxy, C6-10aryloxy, 3-10 membered heterocycle, C(O)Ru (wherein Ru is selected from H, C1-6alkyl, C6-10aryl, C6-10aryl-C1-6alkyl or 3-10 membered heterocycle), C(O)ORv (wherein Rv is selected from H, C1-6alkyl, C6-10aryl, C6-10aryl-C1-6alkyl or 3-10 membered heterocycle), NRxC(O)Rw (wherein Rx is H or C1-6alkyl and Rw is selected from H, C1-6alkyl, C6-10aryl, C6-10aryl-C1-6alkyl or 3-10 membered heterocycle, or Rx and Rw are taken together with the atoms to which they are attached to form a 3 to 10 membered heterocycle) or SO2NRyRz (wherein Ry and Rz are each independently selected from H, C1-6alkyl, C6-10aryl, C3-10heterocycle or C6-10aryl-C1-6alkyl).

In another embodiment, the term "optionally substituted", "optionally substituent" or "substituent" preferably represents halogen, C1-6alkyl, C2-6alkenyl, C2-6alkynyl, C1-6 alkoxy, C2-6alkenyloxy, C2-6alkynyloxy, —NR4OR41, —C(O)NR40R41, —NR40COR41, carboxy, azido, cyano, hydroxyl, nitro, nitroso, —OR40, —SR40, —S(O)0-2R40, —C(O)R40, —C(O)OR40 and —SO2NR4OR41; wherein R40 and R41 are each independently H, C1-6alkyl, C2-6alkenyl or C2-6alkynyl. In still another embodiment, the term "optionally substituted", "optionally substituent" or "substituent" preferably represents halogen, C1-6alkyl, C2-6alkenyl, C1-6 alkoxy, —NR4OR41, —C(O)NR4OR41, —NR40COR41, carboxy, hydroxyl, nitro, —SR40, —S(O)0-2R40, —C(O)R40, —C(O)OR40 and —SO2NR4OR41; wherein R40 and R41 are each independently H, or C1-6alkyl.

In another embodiment, the term "optionally substituted", "optionally substituent" or "substituent" preferably represents halogen, C1-6alkyl, C1-6alkoxy, —NR4OR41, —C(O)NR4OR41, —NR40COR41, carboxy, cyano, hydroxyl, nitro, —S(O)0-2R40, —C(O)R40, —C(O)OR40 and —SO2NR4OR41; wherein R40 and R41 are each independently H, or C1-6alkyl. In still another embodiment, the term "optionally substituted", "optionally substituent" or "substituent" preferably represents halogen, C1-6alkyl, C1-6alkoxy, —NR4OR41, —C(O)NR4OR41, —NR40COR41, carboxy, hydroxyl, —C(O)R40, and —C(O)OR40; wherein R40 and R41 are each independently H, or C1-6alkyl.

In another embodiment, the term "optionally substituted", "optionally substituent" or "substituent" preferably represents halogen, C1-6alkyl, C1-6alkoxy, —NR4OR41, —C(O)NR4OR41, —NR40COR41, carboxy, hydroxyl, —C(O)R40, and —C(O)OR40 wherein R40 and R41 are each independently H, or C1-3alkyl. In still another embodiment, the term "optionally substituted", "optionally substituent" or "substituent" preferably represents F, Cl, C1-3alkyl, C1-3 alkoxy, —NR4OR41, —C(O)NR4OR41, —NR40COR41, carboxy, hydroxyl, —C(O)R40, and —C(O)OR40; wherein R40 and R41 are each independently H, or C1-3alkyl.

The term "independently" means that a substituent can be the same or a different definition for each item.

The compounds as defined herein may include a chiral center which gives rise to enantiomers. The compounds may thus exist in the form of two different optical isomers, that is (+) or (−) enantiomers. All such enantiomers and mixtures thereof, including racemic or other ratio mixtures of individual enantiomers, are included within the scope of the disclosure. The single enantiomer can be obtained by methods well known to those of ordinary skill in the art, such as chiral HPLC, enzymatic resolution and chiral auxiliary derivatization.

It will also be appreciated that the compounds in accordance with the present disclosure can contain more than one chiral centre. The compounds of the present disclosure may thus exist in the form of different diastereomers. All such diastereomers and mixtures thereof are included within the scope of the disclosure. The single diastereomer can be obtained by methods well known in the art, such as HPLC, crystalisation and chromatography.

There is also provided pharmaceutically acceptable salts of the compounds of the present disclosure. What is meant by the term pharmaceutically acceptable salts of the compounds is that they are derived from pharmaceutically acceptable inorganic and organic acids and bases.

For example, conventional non-toxic salts include those derived from inorganic acids such as hydrochloric, hydrobromic, sulfuric, sulfamic, phosphoric, nitric, perchloric and the like, as well as salts prepared from organic acids such as formic, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, benzenesulphonic, naphthalene 2 sulphonic, ethane disulfonic, oxalic, isethionic, trifluoroacetic and the like.

Other acids, while not in themselves pharmaceutically acceptable, may be useful as intermediates in obtaining the compounds of the disclosure and their pharmaceutically acceptable acid addition salts. Salts derived from appropriate bases include alkali metal, alkaline earth metal or ammonium salts. The salt(s) must be "acceptable" in the sense of not being deleterious to the recipient thereof.

The pharmaceutically acceptable salts of the compounds of this disclosure can be synthesized from the compounds of this disclosure which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The term "solvate" means that a compound as defined herein incorporates one or more pharmaceutically acceptable solvents including water to give rise to hydrates. The solvate may contain one or more molecules of solvent per molecule of compound or may contain one or more molecules of compound per molecule of solvent. Illustrative non-limiting examples of hydrates include monohydrate, dihydrate, trihydrate and tetrahydrate or semi-hydrate. In one embodiment, the solvent may be held in the crystal in various ways and thus, the solvent molecule may occupy lattice positions in the crystal, or they may form bonds with salts of the compounds as described herein. The solvate(s) must be "acceptable" in the sense of not being deleterious to the recipient thereof. The solvation may be assessed by methods known in the art such as Loss on Drying techniques (LOD).

It will be appreciated by those skilled in the art that the compounds in accordance with the present disclosure can exist in several different crystalline forms due to a different arrangement of molecules in the crystal lattice. This may include solvate or hydrate (also known as pseudopolymorphs) and amorphous forms. All such crystalline forms and polymorphs are included within the scope of the disclosure. The polymorphs may be characterized by methods well known in the art. Examples of analytical procedures that may be used to determine whether polymorphism occurs include: melting point (including hot-stage microscopy), infrared (not in solution), X-ray powder diffraction, thermal analysis methods (e.g. differential scanning calorimetry (DSC) differential thermal analysis (DTA), thermogravimetric analysis (TGA)), Raman spectroscopy, comparative intrinsic dissolution rate, scanning electron microscopy (SEM).

When there is a sulfur atom present, the sulfur atom can be at different oxidation levels, ie. S, SO, or SO2. All such oxidation levels are within the scope of the present disclosure. When there is a nitrogen atom present, the nitrogen atom can be at different oxidation levels, ie. N or NO. All such oxidation levels are within the scope of the present disclosure.

As defined herein "subject" refers to both human and non-human subjects. Preferably the subject is human.

Without being bound to theory, it is believed that the ability of the synthesized compounds to inhibit multiple key targets involved in CSC and metastasis signaling may provide a significant potential for the management of cancer, in particular metastatic cancers.

As used herein, "treatment" or "treating" refers to at least i) controlling or ameliorating at least one disease described herein, at least for the duration of said treatment. Advantageously, the treatment could i) reduce the occurrences of a further episode, or ii) reduce its severity or iii) prevent occurrences of further episodes, at least for the duration of the therapy. Although not limited to such patients, is expected to be particularly useful to the treatment of patients who have suffered a previous episode associated with diseases described herein, or are otherwise considered to be at increased risk of said diseases.

The expression "cancer" includes, but is not limited to carcinomas, sarcomas, melanomas; lymphoma, leukemia and myelomas; blastomas; germ cell tumor; glioma and other CNS cancers.

In one embodiment, the carcinoma is a cancer of the bladder, breast, cervix, colon, esophagus, kidney, liver, larynx, lung (small and non-small cell lung cancer), oral cavity, ovary, pancreas, pleura, prostate, skin (basal and squamous), stomach, thyroid or uterus.

In one embodiment, the sarcoma is osteosarcoma, chondrosarcoma, liposarcoma, neurosarcoma, rhabdomyosarcoma, Erwing sarcoma or fibrosarcoma.

In one embodiment, the melanoma is malignant melanoma, lentigo maligna melanoma, superficial spreading melanoma, acral lentiginous melanoma, mucosal melanoma, nodular melanoma, polypoid melanoma, desmoplastic melanoma, amelanotic melanoma or soft-tissue melanoma.

In one embodiment, the lymphoma, leukemia and myelomas is acute lymphocytic leukemia, B-cell lymphoma, Burketts lymphoma, Hodgkin and Non-Hodgkin lymphoma, acute and chronic myelogenous leukemias, promyelocytic leukemia or multiple myeloma.

In one embodiment, the blastoma is a blastoma derived from immature "precursor" cells or embryonic tissue, neuroblastoma, retinoblastoma, pleuropulmonary blastoma, nephroblastoma (Wilms tumor) or hepatoblastoma.

In one embodiment, the germ cell tumor is a seminoma, dysgerminoma or teratocarcinoma tumor.

In one embodiment, the glioma and other CNS cancers are ependymomas, astrocytomas, oligodendrogliomas, glioblastomas or oligoastrocytomas.

In one embodiment, the cancer is a breast, prostate, pancreatic cancer, recurrent/metastatic head and neck cancers (thyroid), renal cell carcinoma and melanoma. In a further embodiment, the cancer is metastatic cancer. In one embodiment, the metastatic cells are cells enriched in CSC markers. In a further embodiment, the inhibition of metastasis is in vitro or in vivo. In a further embodiment, the cancer is a refractory cancer. In still a further embodiment, the cancer is metastatic triple negative breast cancer, Her2, luminal, basal-like, inflammatory breast cancer or both refractory and metastatic Her2+ breast cancer.

For the treatment of cancer, chemotherapeutic, immunotherapeutic or immunomodulatory and antiangiogenic agents have been reported. Agents can be used as monotherapy (treatment with one agent) or as combination therapy (simultaneous, separate or sequential treatment with another agent). The treatments may also be combined with radiotherapy.

In another embodiment, the present disclosure provides a combination comprising a therapeutically effective amount of a compound, as defined herein, and a therapeutically effective amount of at least one or more therapeutic agents useful in the method of the present disclosure selected from: Alkylating agents, Anti-metabolites, Plant alkaloids and terpenoids, *Vinca* alkaloids, Podophyllotoxin, Taxanes, Topoisomerase inhibitors, and Cytotoxic antibiotics.

In another embodiment, the present disclosure provides a combination comprising a therapeutically effective amount of a compound, as defined herein, and a therapeutically effective amount of at least one or more therapeutic agents useful in the method of the present disclosure including but not limited to imatinib, paclitaxel, docetaxel, cisplatin, doxorubicine, vinblastine, zoledronate and/or in conjunction with antimetastatic agents, antiangionevic agents such as avastatin, and targeted therapeutics including EGFR, VEGFR, WNT, Aurora, etc. and antiapoptotic compounds such as Velcadetm, agents targeting synthesis of estrogens or estrogen signaling through estrogen receptors including but not limited to arimidex and tamoxifen, agents targeting biosynthesis of androgens or androgen signaling through the androgen receptor including but not limited to bicalutamide, agents targeting HER2 including but not limited to trastuzumab, agents targeting BRAF including but not limited to Vemurafenib, or agents targeting members of the MAP kinase family or their upstream or downstream effector kinases.

It will be clear to a person of ordinary skill that the amounts and/or ratios of therapeutic agents will be readily adjusted. It will be understood that the scope of combinations described herein is not particularly limited, but includes in principle any therapeutic agent useful for preventing or treating the diseases described herein.

It will also be appreciated that the amounts and/or ratios of therapeutic agents for use in treatment will vary not only with the particular agent selected but also with the route of administration, the nature of the condition for which treatment is required and the age and condition of the patient and will be ultimately at the discretion of the attendant physician.

The compounds defined herein can be administered concurrently to the one or more agents used herein in the methods and combinations. The desired doses may conveniently be presented in a single dose or as divided dose administered at appropriate intervals, for example as two, three, four or more doses per day or continuously such as in a perfusion. The compound can be administered on a dosage regimen distinct to the one or more agents used herein in the methods and combinations. Alternatively, the compound can be administered sequentially or concurrently in distinct formulations or in a common formulation.

Pharmaceutical compositions may comprise pharmaceutically acceptable carrier(s) and/or excipient(s). Many pharmaceutically acceptable carrier(s) and/or excipient(s) are known in the art. It will be understood by those in the art that a pharmaceutically acceptable carrier must be compatible with the other ingredients of the formulation and tolerated by a subject in need thereof or liquid preparations, such as oral or sterile parenteral solutions or suspensions. The proportion of each carrier is determined by the solubility and chemical nature of the agent(s), the route of administration, and standard pharmaceutical practice.

In order to ensure consistency of administration, in an embodiment of the present disclosure, the pharmaceutical composition is in the form of a discrete dosage units and may be prepared by any of the methods well known in the art of pharmacy. All methods include the step of bringing into association the active compound with a liquid carrier or solid carrier or both and then, if necessary, shaping the product into the desired formulation.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds and combinations according to the disclosure may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

The following examples are provided to further illustrate details for the preparation and use of the compounds of the present disclosure. They are not intended to be limitations on the scope of the instant disclosure in any way, and they should not be so construed. Furthermore, the compounds described in the following examples are not to be construed as forming the only genus that is considered as the disclosure, and any combination of the compounds or their moieties may itself form a genus.

Examples: Chemistry—Preparation of the Compounds of the Disclosure

Compounds of the present disclosure can be prepared according to the procedures denoted in the following reaction Scheme and examples or modifications thereof using readily available starting materials, reagents, and conventional procedures or variations thereof well-known to a practitioner of ordinary skill in the art of synthetic organic chemistry. Specific definitions of variables in the Schemes are given for illustrative purposes only and are not intended to limit the procedures described.

Scheme 1: General synthesis of the compounds disclosed herein.

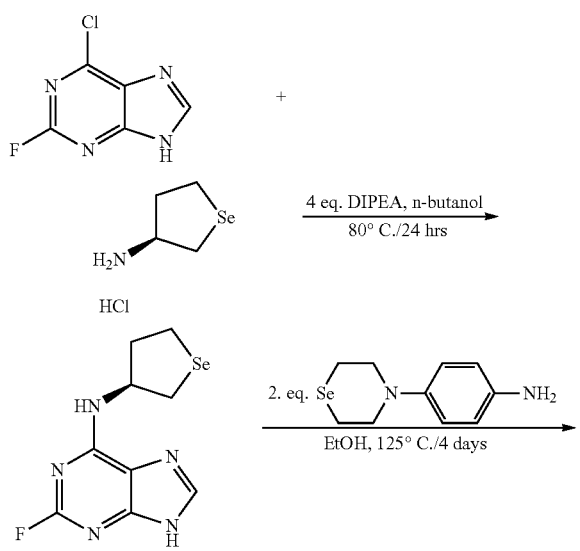

SLLN-15

Example 1: Synthesis of

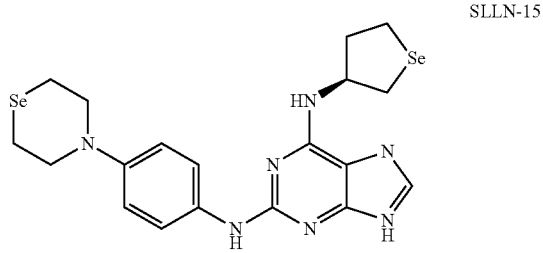 [SMILES: c1nc2nc(Nc3ccc(N4CC[Se]CC4)cc3)nc(N[C@H]3CC[Se]C3)c2[nH]1]

SLLN-15

BRIEF DESCRIPTION 2-(4-Selenomorpholinoanilino-6-[(tetrahydroselenophen-3-yl) amino]-purine (SLLN-15)

The 2-(4-Selenomorpholinoanilino-6-[(tetrahydroselenophen-3-yl) amino]-purine was synthesised in 2 steps according to the previously published protocol (Perreira et al, 2005).

In the first step (S)-tetrahydroselenophen-3-amine hydrochloride was coupled with 6-Chloro-2-fluoropurine (CAS: 1651-29-2, Oakwood Chemical cat. #009088) in presence of 4 equivalents of the base N,N-diisopropylethylamine (DIPEA, CAS: 7087-68-5, Aldrich cat. #D125806) in n-butanol at 80° C. for 24 hrs. The isolated crude product was then coupled with 2 equivalents of 4-selenomorpholinoaniline, in absence of any other base, in ethanol at 125° C. (sealed tube) for 4 days. The pure product was isolated by flash chromatography (silica gel column eluted with 1% to 4% methanol in dichloromethane). The purity and the structure was confirmed by HPLC, 1H NMR, 13C NMR and LC-HRMS.

Chemical Formula: C19H23N7Se2; Exact Mass: 509.03, MW: 507.36, MS MH+: 510.03

1H NMR (500 MHz, DMSO) 12.42-12.31 (1H, m), 8.60 (1H, s), 7.79 (1H, s), 7.66-7.60 (2H, m), 7.31 (1H, s), 6.85-6.78 (2H, m), 4.87-4.77 (1H, m), 3.64-3.60 (4H, m), 3.21-3.15 (2H, m), 2.98-2.91 (1H, m). 2.91-2.82 (2H, m), 2.71-2.67 (4H, m), 2.38-2.30 (1H, m), 2.17-2.07 (1H, m);

13C NMR (126 MHz, DMSO, extracted from HSQC) 136.3, 120.4, 117.0, 52.5, 49.0, 40.1, 36.7, 27.5, 19.1, 15.4.

The other compounds may be synthesised using the same approach and synthesis steps with appropriate starting materials.

Examples: Biology

The following examples show the anti-proliferative function of SLLN-15, as a representative compound of the compounds disclosed herein, on a panel of TNBC cells in vitro and in vivo. The compound functions by inducing autophagy via the Akt/mTOR pathway. SLLN-15 promoted Aurora A kinase degradation, resulting in blockade of Akt/mTOR signaling, thereby activating cytostatic autophagy in breast cancer cells. These results support the potential therapeutic utility of autophagy activation for cancer (such as TNBC) management.

Materials and Methods

Antibodies and Reagents

Antibodies used were as follows: anti-β-actin, anti-p62 and anti-LC3B (Santa Cruz); anti-phospho-Aurora A(Thr288)/B(Thr232)/C(Thr198), anti-Aurora A, anti-Aurora B, anti-cleaved PARP, anti-cleaved caspase3, anti-Bcl-2, anti-p-S473-Akt, anti-Akt, anti-p-S2448-mTOR, anti-mTOR, anti-p-T421/S424-p70S6K, anti-p70S6K, anti-p-S240/244-S6, anti-S6, anti-p-T37/46-4EBP1, anti-4EBP1, Atg5 and Atg7 (cell signaling), anti-Beclin1 (Santa Cruz) anti-LC3B (Novus); anti-GAPDH and anti-FLAG (sigma). Anti-mouse and anti-rabbit IgG-peroxidase-conjugated secondary antibodies for Western blot assays were from Bio-Rad. Alexa Fluor 594 and 488 conjugated secondary antibodies were from Life Technology. MG-132 was from Calbiochem. Chloroquine (CQ), vorinostat (SAHA), DAPI and 3-methyladenine (3-MA) were from Sigma-Aldrich.

Cell Culture

The breast cancer cell lines MDA-231, BT-20, 4T1, MCF-7, MDA-MB-468, SKBR-3 and HEK293T cells were all obtained from the American Type Culture Collection. MDA-MB-468 was cultured in L-12 medium and all other cell lines were maintained in RPMI 1640 (Fisher) supplemented with 10% FBS and with 1% penicillin and streptomycin antibiotics.

Plasmids Construction pCDNA3-HA-Akt (plasmid #73408) was obtained from Addgene. Plasmids used for transient transfection include pCMV-Aurora A and pCMV-Aurora B generated by PCR and cloned into BamHI/Xho I site of pCMV-Tag-4A vector. The primers sequence for Aurora A are: sense: 5'-CGGGATCCATGGACCGATCTAAAGAAAAC-3' (SEQ ID NO: 1); antisense: 5'-CCGCTCGAGAG ACTGTTTGCTAGCTGATTC-3' (SEQ ID NO: 2) and for Aurora B are: sense: 5'-.CGGGATCCATGAGCCGC TCCAATGTCC-3' (SEQ ID NO: 3); antisense: 5'-CCGCTCGAGGGCGACAGATTGAAGGGC-3' (SEQ ID NO: 4). All plasmids were transfected into BT-20 cells using Lipofectamine LTX and PLUS reagents (Invitrogen) according to the manufacturer's instructions.

siRNA Gene Knockdown

Non-targeted siRNA sequence: sense, 5'-UU-CUCCGAACGUGUCACGUdTdT-3' (SEQ ID NO: 5); antisense, 5'-ACGGUGACACGUUCGGAGAAdTdT-3' (SEQ ID NO: 6), Beclin1 siRNA sequences: sense, 5'-CUCAAGUUCAUGCUGACGAAUUdTdT-3' (SEQ ID NO: 7) antisense, 5'-UUCGUCAGCAUGAACUUGAGdTdT-3' (SEQ ID NO: 8), Atg5 siRNA sequence: sense, 5'-AGAUUGAAGGAUCAACUAUUUdTdT-3' (SEQ ID NO: 9); antisense, 5'-AAUAGUUGAUCCUUCAAUC-UUUdTdT-3' (SEQ ID NO: 10), Atg7 siRNA sequence: sense, 5'-GCCUGCUGAGGAGCUCUCCAUUdTdT-3' (SEQ ID NO: 11); antisense, 5'-UGGAGAGCUC-CUCAGCAGGC UU-3' (SEQ ID NO: 12) were synthesised from Dharmacon. Control siRNA or target siRNA oligonucleotides were expressed in cells by incubated with INTERFERin (Polyplus transfection) in serum-free RPMI medium according to the manufacturer's instruction.

Measurement of Cell Viability

The short-term effects of SLLN-15 on tumor cell growth were assessed using the 3-(4,5-dimethylthiazol-2-yl)-2,5-diphenylte-trazolium bromide (MTT; Sigma) assay. Cells were seeded at a density of 5000 cells/well in a 96-well plate and treated with SLLN-15 as indicated concentration or DMSO for 24 hours. MTT solution (5 mg/ml in RPMI 1640 medium) was added (20 μl/well), and plates were incubated for 4 hours in dark at 37° C., then the purple formazan crystals were then dissolved in 100 μl MTT solvent (4 mM HCl and 0.1% NP-40 in isopropanol). The plates were read on FLUOstar OPTIMA microplate reader (BMG Labtech, Ortenberg, Germany) at 570 nm. Assays were performed in triplicate on three independent experiments.

Colony Formation Assay

The long-term effects of SLLN-15 on tumor cell growth were assessed using the colony formation assay. Cells were trypsinized and plated in triplicate wells in 12-well plate (500 cells/well). After six hours of incubation, cells were treated with the indicated concentrations of SLLN-15 or DMSO. 7 days after the cells plated and treated, they were washed and stained with a mixture of 0.05% w/v crystal violet and 6% v/v glutaraldehyde, and the colonies >100 μm in diameter were counted using a colony counter (Oxford Optronix Gelcount, Inc., Milton Park, Abingdon, UK).

BrdU Labeling Assay

The proliferation effects of SLLN-15 were assessed using the bromodeoxyuridine (BrdU) Cell proliferation Assay Kit (Biovision). Cells were seeded at a density of 5000 cells/ well in a 96-well plate and treated with SLLN-15 or rapamycin (Cayman chemical) as indicated concentration or DMSO for 24 hours. The plates were read on FLUOstar OPTIMA microplate reader (BMG Labtech, Ortenberg, Germany) at 450 nm. Assays were performed in triplicate on three independent experiments.

Flow Cytometry

Cells were seeded into six-well plates and treated with the indicated concentration of SLLN-15 for 24 hours. After harvesting, cells were fixed in 80% methanol at −20° C. overnight. The fixed cells were washed twice with cold phosphate-buffered saline (PBS), incubated for 1 hour with 0.1% Triton X-100 and 0.5 μg/ml RNase A, and then stained with propidium iodide (PI) (Sigma) at a final concentration of 10 μg/ml in the dark at 4° C. until analysis. The fluorescent signal was detected through the FL-2 channel using FACSCalibur flow cytometry (Becton Dickson), and the proportion of DNA in various phases was analyzed using FCS Express version 3.0 (De novo Software, Glendale, California, USA)

Electron Microscopy

BT-20 and MDA-MB-231 cells were fixed in situ for an hour at 4° C. with 4% glutaraldehyde in 0.1M sodium cacodylate (Caco) buffer, pH7.2. Cells were washed and scrapped off the plates, in Caco buffer, and pelleted by low speed centrifugation. The pellets were post-fixed with 1% OsO4 in Caco buffer for an hour at 4° C. and then dehydrated in graded series of ethanol and embedded in Epon44. Ultrathin sections were obtained using a Reichert Ultracut ultramicrotome and mounted on naked nickel grids. Sections were stain with 2% aqueous uranyl acetate and lead citrate. Examination was performed with a Philips CM100 transmission electron microscope. Electron microscopy studies were carried out at the University of Montreal Imaging Facility.

Immunoblotting Assay

Sub-confluent cells were washed with PBS, lysed in RIPA buffer (50 mM Tris-HCl at pH7.5, 150 mM sodium chloride, 1% tritonX-100, 0.1% SDS, 2 mM EDTA and 25 mM sodium fluoride) supplemented with 1 mM PMSF and protease inhibitor cocktail (Roche) for 10 min on ice and centrifuged (13,000 rpm at 4° C. for 20 min) to separate cell lysate. Cell lysate (50 μg protein, as measured by the Bradford protein assay) was then added with SDS sample buffer (Tris at pH 6.8, 20% glycerol, 5% SDS, bromophenol blue and β-mercaptoethanol) and boiled for 5 min. Samples were then resolved through 13% SDS-PAGE gels, transferred to nitrocellulose membrane, blotted with specific first antibodies at different dilution in cold room overnight, and then amplified with horseradish peroxidase-conjugated secondary antibodies for 1 hour in room temperature and enhanced by chemiluminescence detection system.

Immunofluorescence Microscopy

Cells were grown on 18-mm cover glass, placed in 6-well culture plate for 24 hours, rinsed in PBS, fixed with 4% paraformaldehyde/PBS for 10 min, washed twice in PBS with 0.2% TritonX-100, blocked in PBS with 0.2% Triton X-100 containing 1% BSA (Bioshop) and incubated with primary antibodies overnight at 4° C. (all in 1/100 diluted in blocking solution). The cells were washed with PBS containing 0.2% TritonX-100 and subsequently incubated with Alexa Fluor 488-labelled, Alexa Fluor 594-labelled, or Alexa Fluor 647-labelled secondary antibodies (all were used at 1/500 dilution in blocking solution) for 1 hour in room temperature. The nuclei were stained with DAPI (0.1 μg/ml) for 5 min before mounted with aqueous mounting medium. Cells were imaged using WaveFX spinning disk confocal microscope system (Quorum Technologies INC.). Images shown are representative of three independent experiments.

In Vivo Allograft Model of Breast Cancer

All experiments were carried out according to protocol number 4101 of the McGill University Animal Care Committee. Mouse mammary carcinoma 4T1 cells (1×106 cells/each mouse) were transplanted into the mammary fat pad of BALB/c mice. Once a palpable tumor was present mice were treated intraperitoneal with either vehicle or SLLN-15 (20 mg/kg), 3 times a week. Tumor size was measured using a caliper, and tumor volume was calculated as n/6 (length× width2). Mice were sacrificed 40 days after transplanting. Tumor tissues were isolated and fixed in 10% formalin. The lungs were fixed in 10% Bouin's fixative and lung metastatic nodules on the surface were counted using a stereomicroscope (Optimax; Leica).

Statistical Analysis

All data present as mean±SEM using Prism 6.0 (GraphPad Software). Statistical significant was analyzed using unpaired two-tailed Student's t-test. Data were deemed to be statistically significant if $P<0.05$.

Results

SLLN-15 Inhibits TNBC Cell Growth In Vitro and In Vivo

Figure 1B:
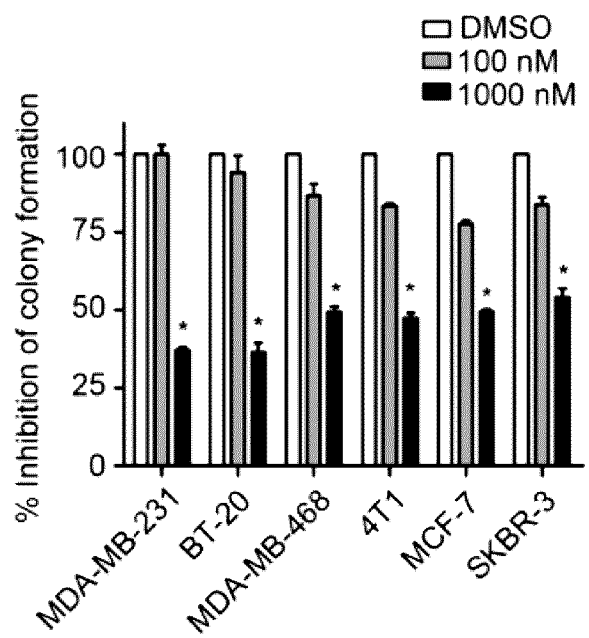
FIG. 1B is a bar graph representing the long-term cell viability of a panel of breast cancer cells measured via colony formation assay, after treatment compared to a control.
Figure 1C:
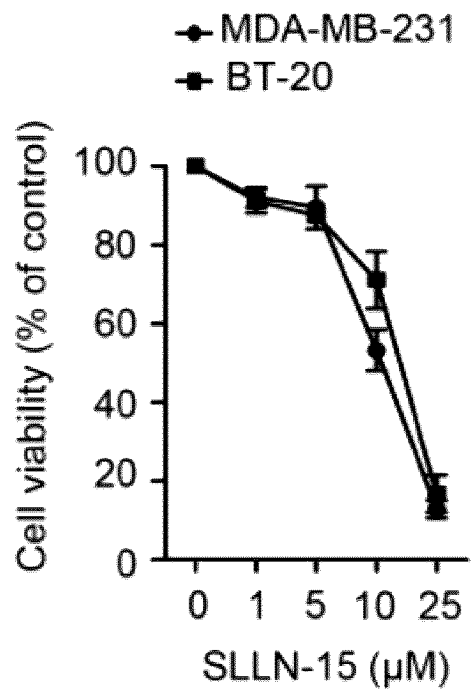
FIG. 1C represents the short-term cell viability assay (MTT) of MDA-MD-231 and BT20 cells after treatment as compared to a control.

Within our quest to develop effective novel anti-cancer drug for TNBCs, we designed and synthesized a library of compounds derived from seleno-purine scaffolds. A high-throughput screening of major classes of kinases and enzymes involved in carcinogenesis identified a 4-selenomorpholinophenyl- and tetrahydroselenophene-substituted diamino-purines, namely SLLN-15 (FIG. 1A), as a potent small molecule capable of inhibiting TNBC cells. SLLN-15 was able to equally inhibit the colony formation abilities of several breast cancer cell lines, namely TNBC cells MDA-MB-231, BT20, MDA-MD468 and 4T1, MCF-7 (ER+, PR+) and SKBR3 (Her2+) (FIG. 1B). Subsequent cell-based assays confirmed this small molecule to inhibit the proliferation of two TNBC cell lines, BT-20 and MDA-MB-231. As shown in FIG. 1C, SLLN-15 treatment for 24 hours markedly decreased overall cell viability of breast cancer cells in a dose-dependent manner. Under this condition, light microscopy revealed that SLLN-15 induced obvious morphological changes compared to control cells, with the appearance of more detached and shrunken cells (FIG. 5I).

Figure 1D:
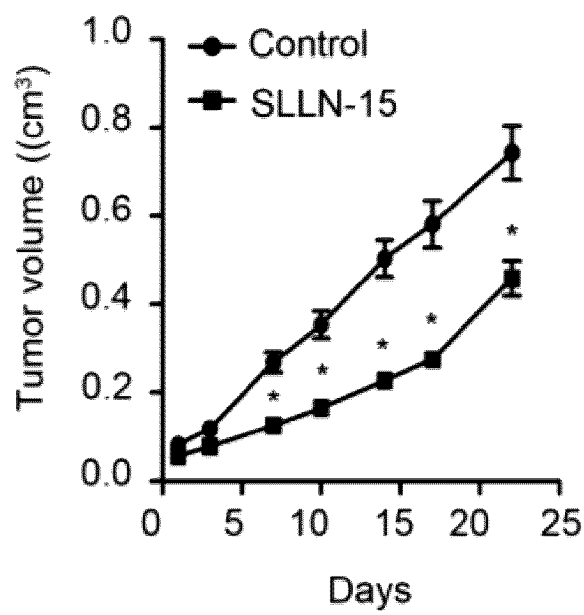
FIG. 1D is a graph demonstrating the primary tumor volume from BALB/c mice implanted with mouse mammary carcinoma 4T1 cells and treated with either vehicle or SLLN-15 (20 mg/kg).
Figure 1E:
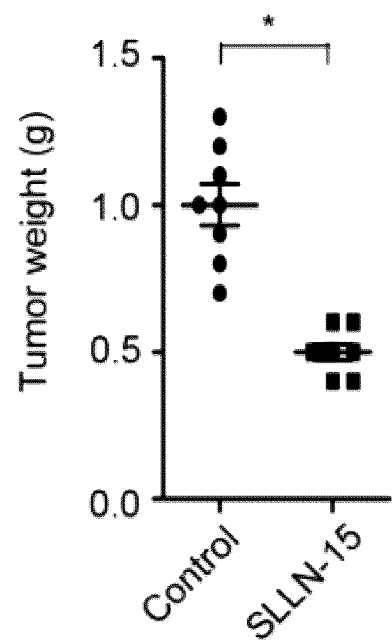
FIG. 1E is a graph demonstrating the primary tumor weight from BALB/c mice implanted with mouse mammary carcinoma 4T1 cells and treated with either vehicle or SLLN-15 (20 mg/kg).
Figure 1F:
FIG. 1F is a graph demonstrating the # of surface lung metastases observed in BALB/c mice implanted with mouse mammary carcinoma 4T1 cells and treated with either vehicle or SLLN-15 (20 mg/kg).
Figure 1F:
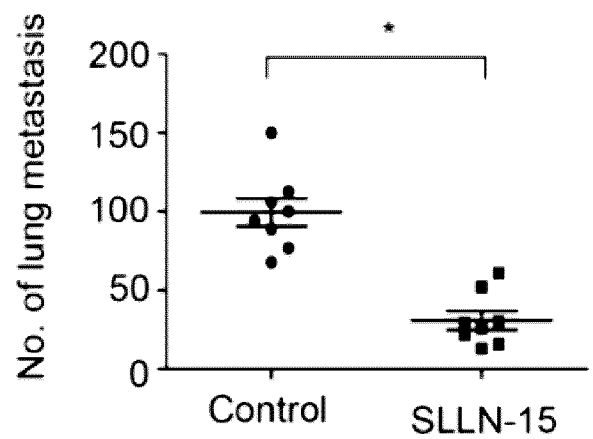

To further evaluate the in vivo efficacy of SLLN-15 in breast cancer, we employed an orthotopic mouse breast cancer model by implanting 4T1 cells (triple-negative breast carcinoma) into the mammary fat pad of BALB/c mice. As shown in FIGS. 1D and E, tumor allografts from mice treated with 30 mg/kg of SLLN-15 given PO, grew at a slower rate compared to mice treated with vehicle, as revealed by the reduced tumor volumes and weights. Furthermore, significant inhibition of the number of lung metastases was observed in mice treated with SLLN-15, compared with vehicle-treated animals (FIG. 1F). Taken together, these data indicate that SLLN-15 not only inhibits the growth of TNBC in vitro and in vivo, but also TNBC cell progression to metastases.

Treatment of SLLN-15 Stimulates Autophagy in TNBC Cells

Figure 2A:
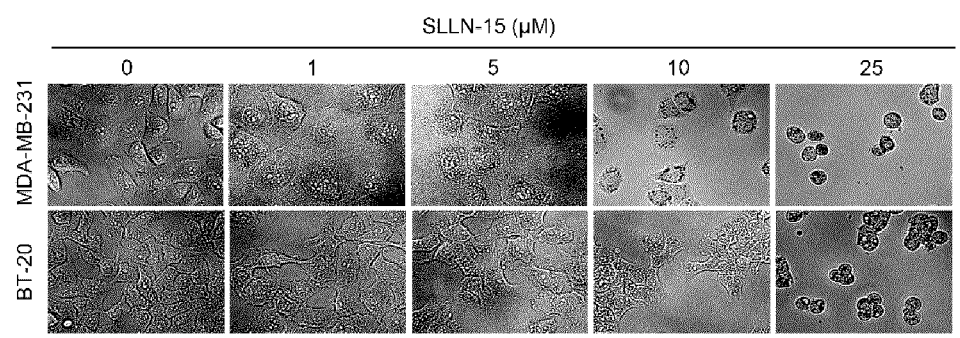
FIG. 2A is a western blot of SLLN-15 or DMSO treated MDA-MB-231 and BT-20 cells immunoblotted with antibodies against LC3B and GAPDH (internal control).
Figure 2A:
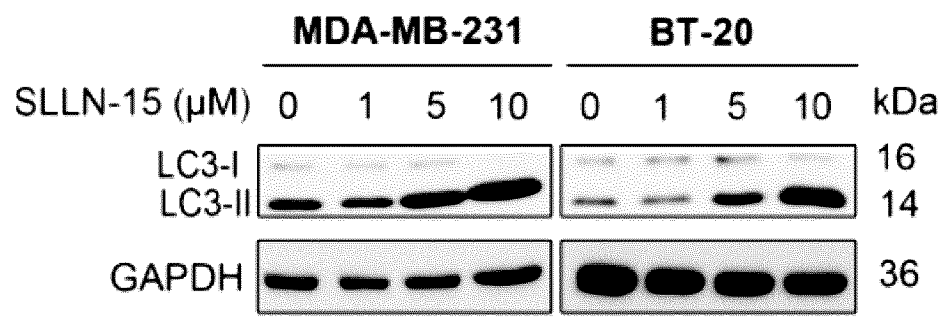
Figure 2B:
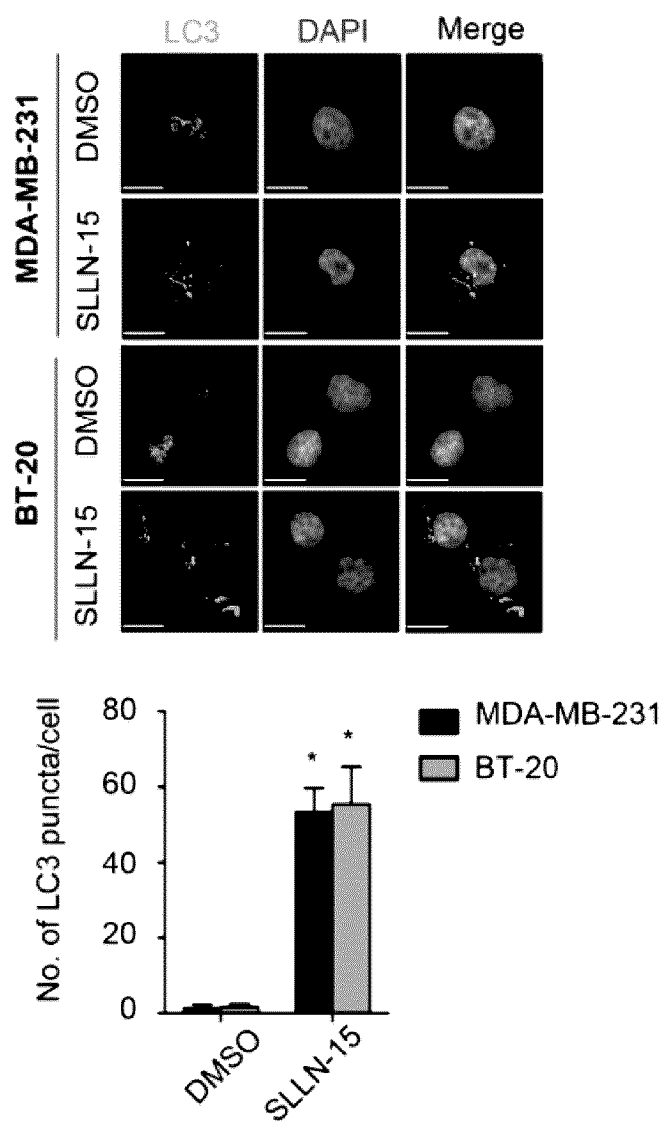
FIG. 2B demonstrates the immunohistochemistry of SLLN-15 or DMSO treated MDA-MB-231 and BT-20 cells stained with anti-LC3 antibody (green) and with DAPI (blue) demonstrating the average number of LC3 puncta per cells.

In order to determine whether SLLN-15 affects autophagy in triple-negative breast cancer cells, we first investigated its effect on the formation of autophagosomes by detecting the conversion of LC3-I to lipidated LC3-II and the distribution of endogenous LC3 puncta, both classic markers of autophagy regulation (Klionsky D J et al. Guidelines for the use and interpretation of assays for monitoring autophagy (3rd edition) Autophagy 2016; 12:1-222). As such, SLLN-15 treatment caused the induction of autophagy as evidenced by increased LC3-II conversion and LC3 puncta, in a dose-dependent manner (FIGS. 2A and B). Next, we investigated the expression level of other autophagy markers upon SLLN-15 treatment, including p62/SQSTM1, Beclin1, Atg5 and Atg7, however no changes in their expression levels were observed (FIG. S2). In order to visualize the induction of autophagy by SLLN-15, we then used transmission electron microscopy. As shown in FIG. 2C, many of the MDA-MB-231 and BT-20 cells treated with SLLN-15 displayed an accumulation of double or multi-membrane structures, indicative of autophagic vacuoles.

Effect of SLLN-15 on Autophagic Flux in TNBC Cells

Figure 3A:
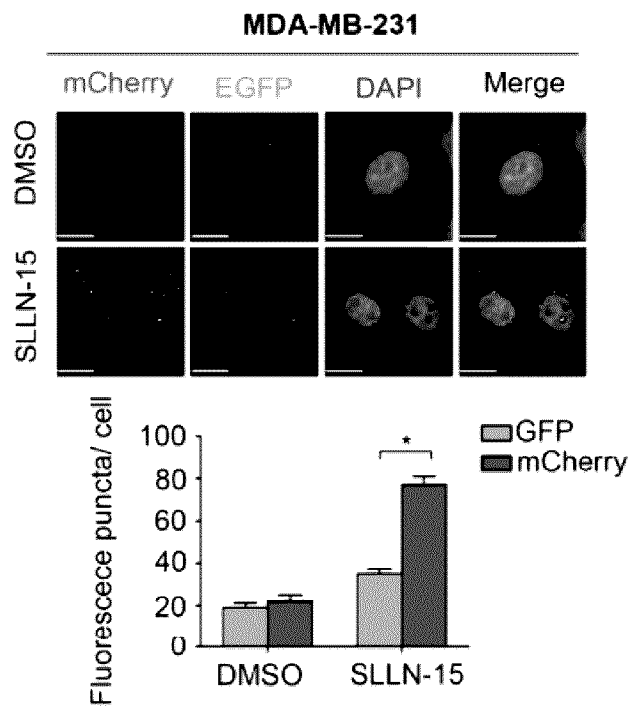
FIG. 3A demonstrates the autophagy flux in MDA-MB-231 cells treated with SLLN-15 or DMSO. Cells were transfected with mCherry-GFP tandem fluorescent-tagged LC3 (mCherry-GFP-LC3).
Figure 3B:
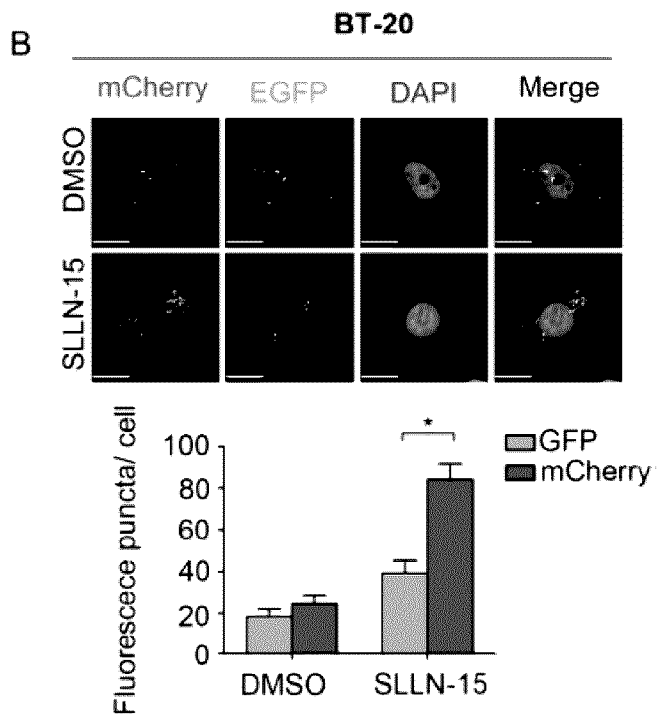
FIG. 3B demonstrates the autophagy flux in BT20 cells treated with SLLN-15 or DMSO. Cells were transfected with mCherry-GFP tandem fluorescent-tagged LC3 (mCherry-GFP-LC3).
Figure 3C:
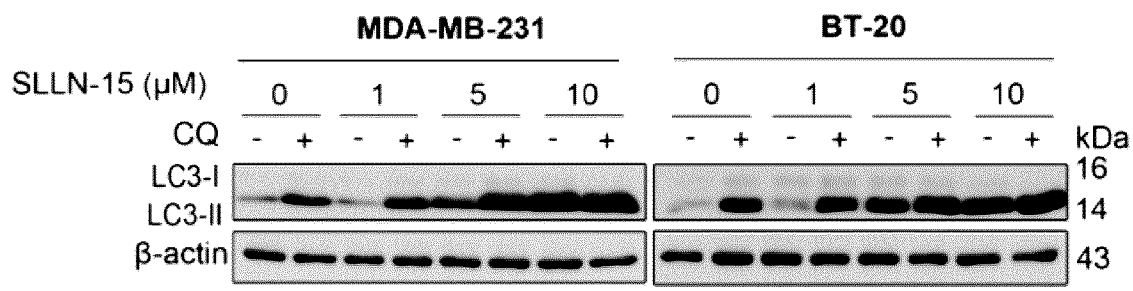
FIG. 3C is a western blot of MDA-MB-231 and BT-20 cells treated with DMSO or SLLN-15 alone or in combination with chloroquine (CQ) immunoblotted with antibodies against LC3B and β-actin.
Figure 3D:
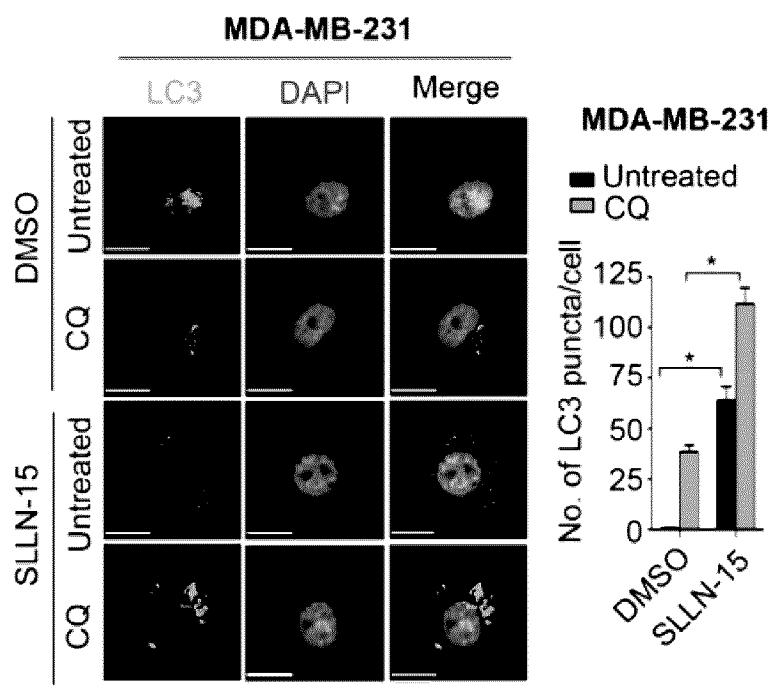
FIG. 3D demonstrates the immunohistochemistry of MDA-MB-231 cells treated with either DMSO or SLLN-15 in the presence or absence of CQ stained with anti-LC3 antibody (green) and with DAPI (blue).
Figure 3E:
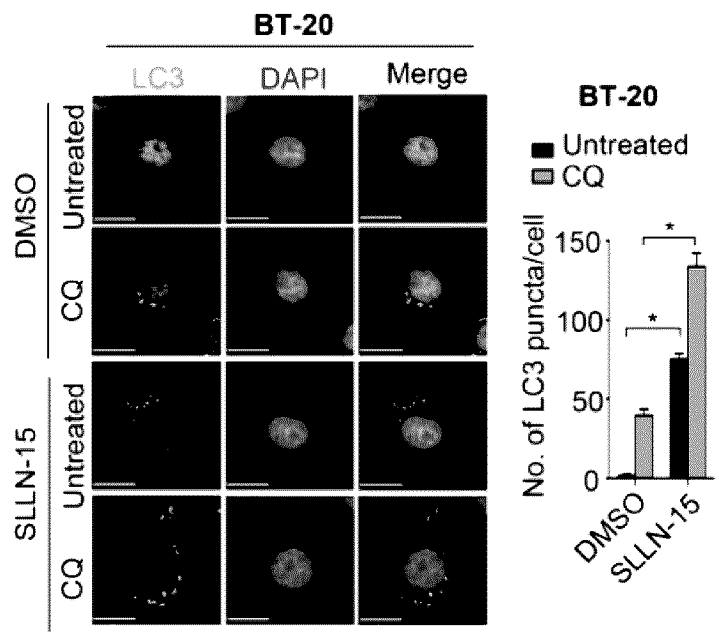
FIG. 3E demonstrates the immunohistochemistry of BT20 cells treated with either DMSO or SLLN-15 in the presence or absence of CQ stained with anti-LC3 antibody (green) and with DAPI (blue).

Distinguishing between autophagy inducers and inhibitors is a delicate task, since both cause a build-up of LC3-II and LC3-positive puncta (Mizushima N, et al. Methods in mammalian autophagy research Cell 2010; 140:313-26). Therefore, to further determine the role of SLLN-15 on autophagy, we next investigated its impact on autophagic flux using a tandem monomeric mCherry-GFP-tagged LC3. We found increased formation of yellow fluorescence (autophagosomes) and red fluorescence (autophagolysosomes) in both MDA-MB-231 and BT-20 cells (FIGS. 3A and B). SLLN-15-induced autophagic flux was further examined in the presence or absence of the autophagosome-lysosome fusion inhibitor, chloroquine (CQ) (Mizushima N, et al. Methods in mammalian autophagy research Cell 2010; 140:313-26). As shown in FIG. 3C, enhanced LC3-II/LC3-I ratio was observed in both MDA-MB-231 and BT-20 cells treated with SLLN-15 combined with CQ, as compared to SLLN-15 alone. This observation was further confirmed by detecting the number of LC3 puncta in SLLN-15-treated cells, as compared to SLLN-15 combined with CQ (FIG. 3D). Taken together, these results suggest that SLLN-15 function as an autophagy inducer in TNBC cells.

SLLN-15 Downregulates the mTOR Pathway

Figure 4A:
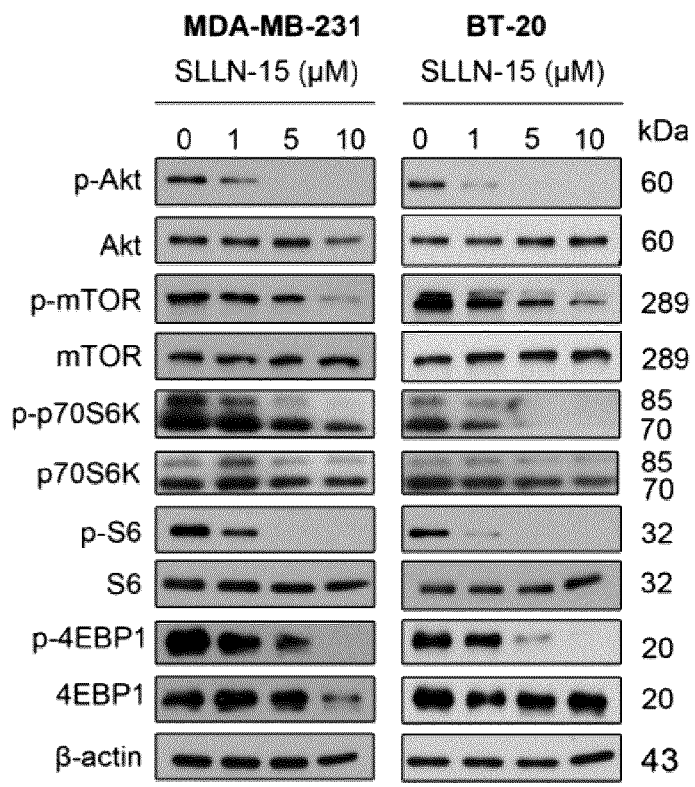
FIG. 4A is a western blot of MDA-MB-231 and BT-20 cells treated with either DMSO or indicated concentrations of SLLN-15 immunoblotted with anti-p-S473-Akt, anti-Akt, anti-p-S2448-mTOR, anti-mTOR, anti-p-T421/S424-p70S6K, anti-p70S6K, anti-p-S240/244-S6, anti-S6, anti-p-T37/46-4EBP1 and anti-4EBP1 and β-actin antibodies.
Figure 4B:
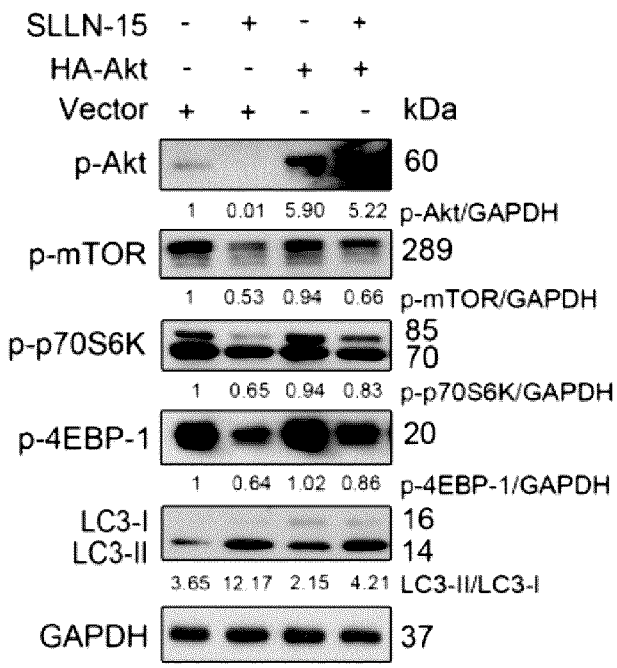
FIG. 4B is a western blot of BT-20 cells transfected with an empty vector (pcDNA3-HA) or pcDNA3-HA-Akt plasmid treated with SLLN-15 immunoblotted with antibodies against p-S473-Akt, p-S2448-mTOR, p-T421/S424-p70S6K, p-T37/46-4EBP1, LC3B and anti-GAPDH.
Figure 4C:
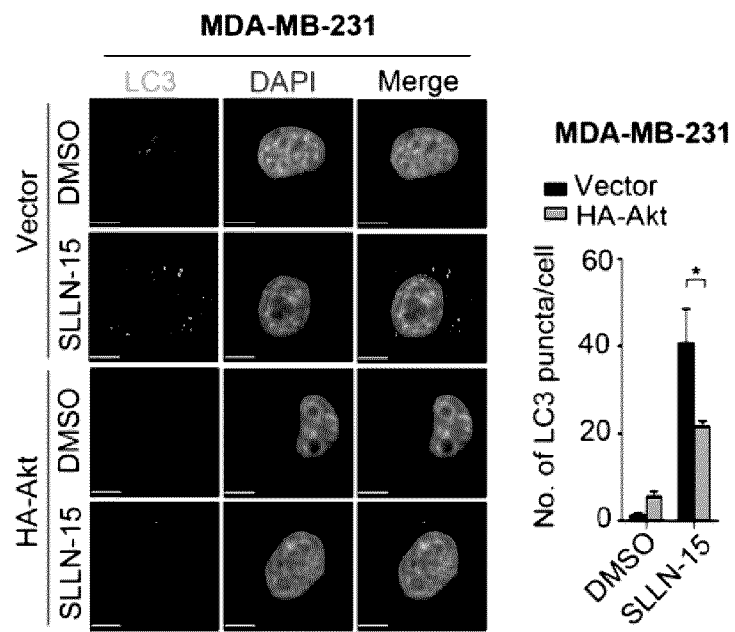
FIG. 4C demonstrates the immunohistochemistry of MDA-MB-231 cells transfected with an empty pcDNA3-HA (vector) or pcDNA3-HA-Akt plasmid treated with SLLN-15 and stained with anti-LC3 antibody (green) and with DAPI (blue).
Figure 4D:
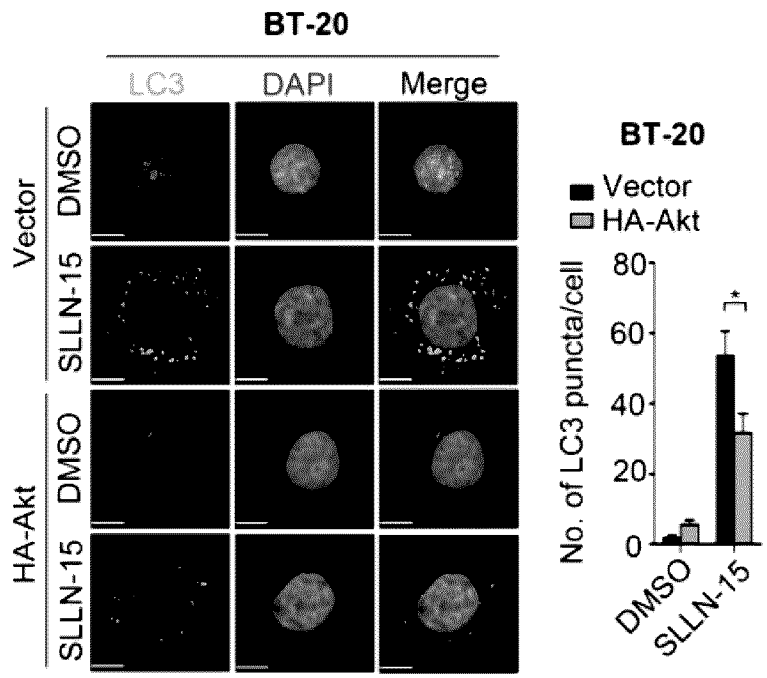
FIG. 4D demonstrates the immunohistochemistry of BT20 cells transfected with an empty pcDNA3-HA (vector) or pcDNA3-HA-Akt plasmid treated with SLLN-15 and stained with anti-LC3 antibody (green) and with DAPI (blue).

The PI3K/Akt/mTOR pathway is a well-established pathway that is frequently activated in cancer cells and acts as a key negative regulator of autophagy (Schmelzle T et al. TOR, a central controller of cell growth Cell 2000; 103: 253-62; Shi J et al. IL10 inhibits starvation-induced autophagy in hypertrophic scar fibroblasts via cross talk between the IL10-IL10R-STAT3 and IL10-AKT-mTOR pathways Cell Death Dis 2016; 7:e2133). Hence, we examine the role of the Akt/mTOR pathway in SLLN-15-treated MDA-MB-231 and BT-20 cells. As shown in FIG. 4A, SLLN-15 treatment strongly inhibited a panel of regulators in the Akt/mTOR pathway, as evidenced by decreased phosphorylation levels of Akt, mTOR, p70S6K, S6 and 4EBP1, in both MDA-MB-231 and BT-20 cells. To further identify the role of Akt in SLLN-15-induced autophagy, we transiently transfect BT-20 cells with pcDNA-HA-Akt plasmids to restore SLLN-15-induced Akt/mTOR inhibition. We found overexpression of Akt significantly restored the inhibition of downstream regulators, including p-mTOR, p-p-70S6K and p-4EBP-1 (FIG. 4B). Moreover, Akt activation reduced LC3-II conversion (FIG. 4B) and LC3 puncta accumulation in MDA-MB-231 and BT-20 cells (FIGS. 4C and D), indicating that the induction of autophagy caused by SLLN-15 was in fact via the Akt/mTOR pathway.

The Anticancer Activity of SLLN-15 is Achieved Via the Autophagic Pathway

Figure 5A:
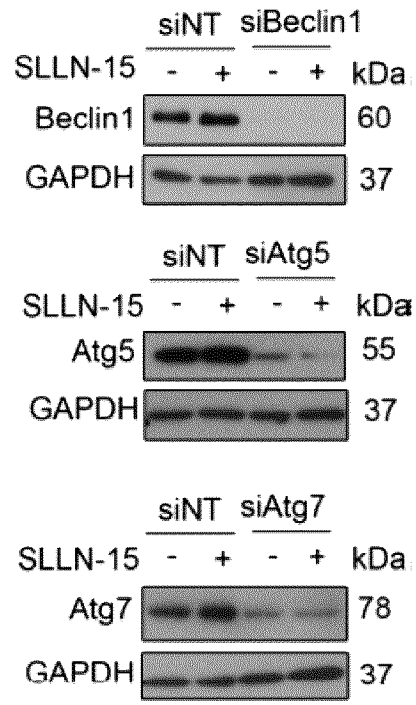
FIG. 5A is a western blot of BT-20 cells transfected with siRNA against control, Beclin1, Atg5 or Atg7 and treated with either DMSO or SLLN-15 immunoblotted with antibodies against Beclin1, Atg5, Atg7 and anti-GAPDH.
Figure 5B:
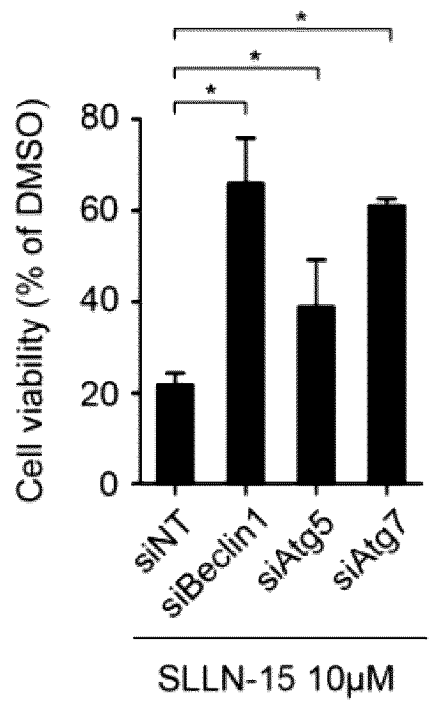
FIG. 5B represents the short-term cell viability assay (MTT) BT20 cells transfected with siRNA against control, Beclin1, Atg5 or Atg7 and treated with DMSO or SLLN-15, as compared to control.
Figure 5C:
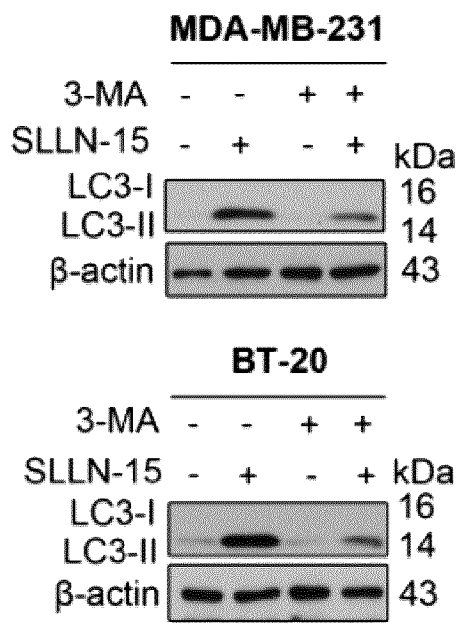
FIG. 5C is a western blot of MDA-MB-231 and BT-20 cells treated with either DMSO or indicated concentrations of SLLN-15 alone or in combination with 3-methyladenine (3-MA), immunoblotted with antibodies against LC3B and β-actin.
Figure 5D:
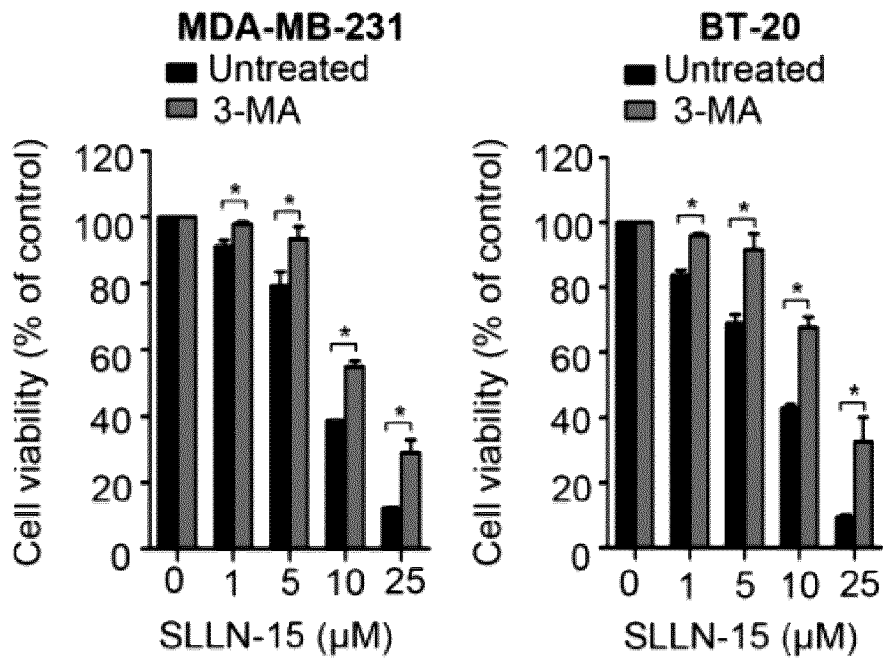
FIG. 5D represents the short-term cell viability assay (MTT) of MDA-MB-231 and BT-20 cells with either DMSO or indicated concentrations of SLLN-15 alone or in combination with 3-methyladenine (3-MA).
Figure 5E:
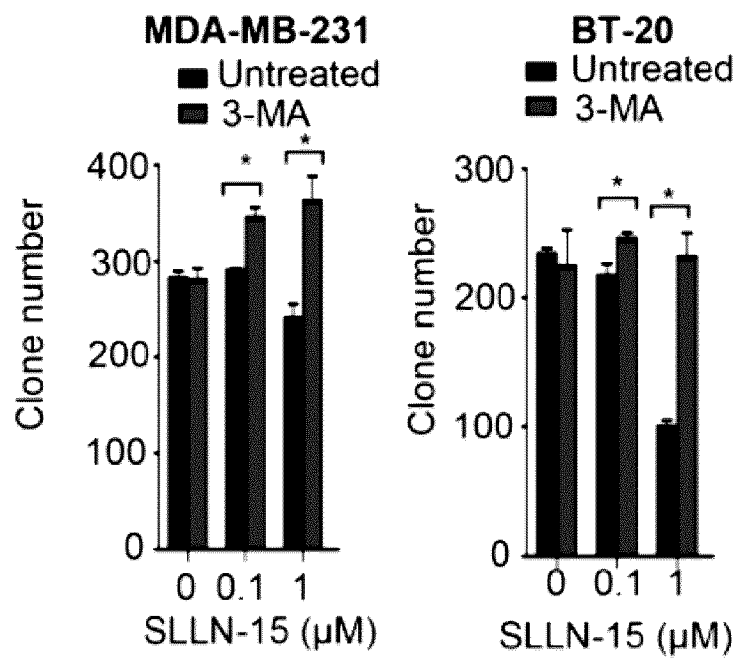
FIG. 5E is a bar graph representing the long-term cell viability of MDA-MB-231 and BT-20 cells treated with either DMSO or indicated concentrations of SLLN-15 alone or in combination with 3-methyladenine (3-MA).

To determine whether the anticancer effect of SLLN-15 in breast cancer cells was through the induction of autophagy, we first used siRNA to silence the expression of key autophagy regulators Beclin1, Atg5 and Atg7, followed by treatment with SLLN-15 (FIG. 5A). As shown in FIG. 5B, knockdown of Beclin1, Atg5 or Atg7 restored cell viability in SLLN-15 treated BT-20 cells, as compared with scrambled siRNA. Moreover, to explore the link between the inhibition of autophagy and SLLN-15 induced cytotoxicity, cells were treated in the presence or absence of the autophagy inhibitor 3-methyladenine (3-MA), a class III phosphatidylinositol 3-kinase (PtIns3K) inhibitor, that prevents formation of autophagosomes (Klionsky D J et al. Guidelines for the use and interpretation of assays for monitoring autophagy in higher eukaryotes Autophagy 2008; 4:151-75), followed by treatment with SLLN-15. The combination of SLLN-15 with 3-MA significantly decreases LC3-II/I ratio (FIG. 5C). Remarkably, autophagy inhibition by 3-MA rescued both short-term and long-term cell viability from SLLN-15-induced cell death as demonstrated in the MTT and clonogenic assay (FIGS. 5D and E). These results suggest that induction of autophagy promotes autophagy-mediated cytotoxicity in MDA-MB-231 cells and BT-20 cells in response to SLLN-15, and inhibition of autophagy counteracts the cytotoxic effect of SLLN-15 in these cells.

SLLN-15 Regulates TNBC Cell Growth but not Apoptosis

Figure 6A:
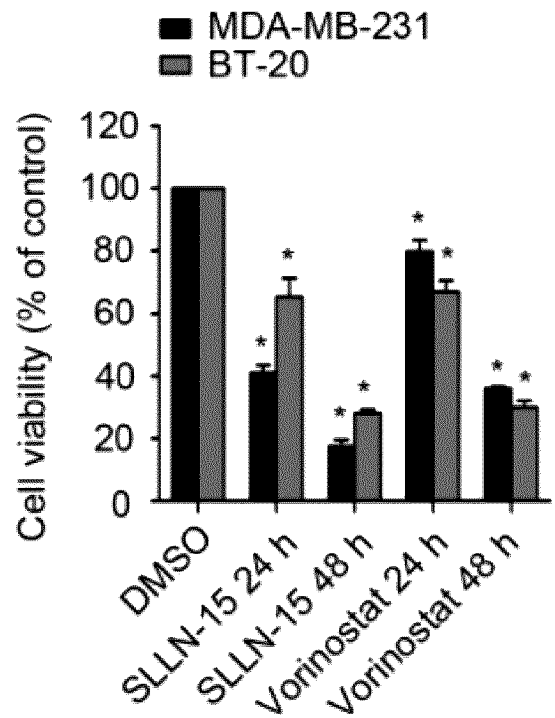
FIG. 6A represents the short-term cell viability assay (MTT) of MDA-MB-231 and BT-20 cells treated with vorinostat, SLLN-15 or DMSO.
Figure 6B:
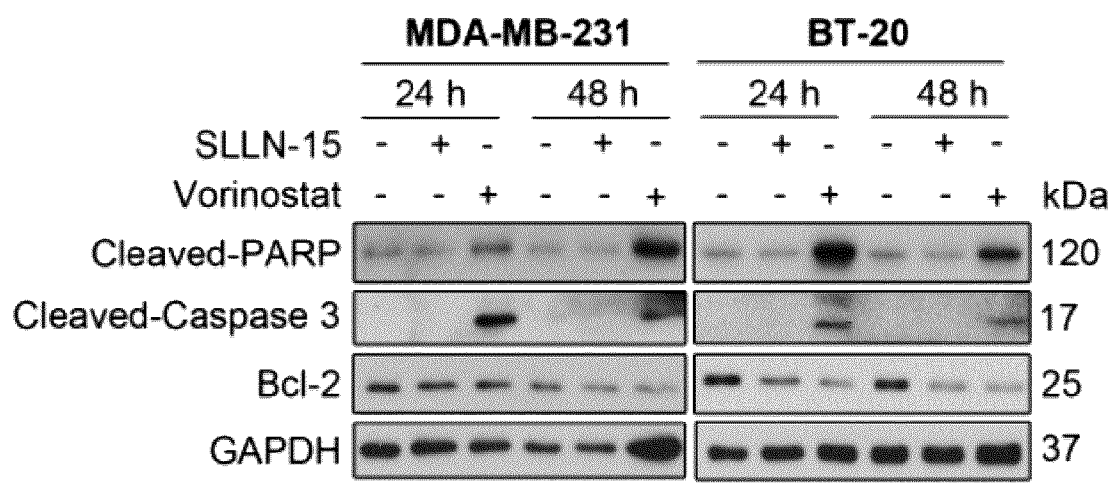
FIG. 6B is a western blot of MDA-MB-231 and BT-20 cells treated with vorinostat, SLLN-15 or DMSO, immunoblotted with antibodies against cleaved-PARP, cleaved-caspase-3, Bcl-2 and GAPDH.

Considering apoptosis is the major form of cell death induced by chemotherapeutic agent, we seek to identify whether the anticancer effect of SLLN-15 was mediated via apoptosis in breast cancer cells. Therefore, we conducted the MTT assay comparing SLLN-15 and vorinostat, an histone deacetylase (HDAC) inhibitor that can induce apoptosis in cancer cells (Kumagai T et al. Histone deacetylase inhibitor, suberoylanilide hydroxamic acid (Vorinostat, SAHA) profoundly inhibits the growth of human pancreatic cancer cells Int J Cancer 2007; 121:656-65). As shown in FIG. 6A, both SLLN-15 and vorinostat treatment markedly decreased cell viability in MDA-MB-231 and BT-20 cells in time-dependent manner. Western blot analysis showed that indicators of apoptosis, including upregulation of cleaved-PARP and cleaved-caspase 3 and downregulation of Bcl-2, were only detected in vorinostat treated cells but not SLLN-15 treated cells (FIG. 6B).

Figure 6C:
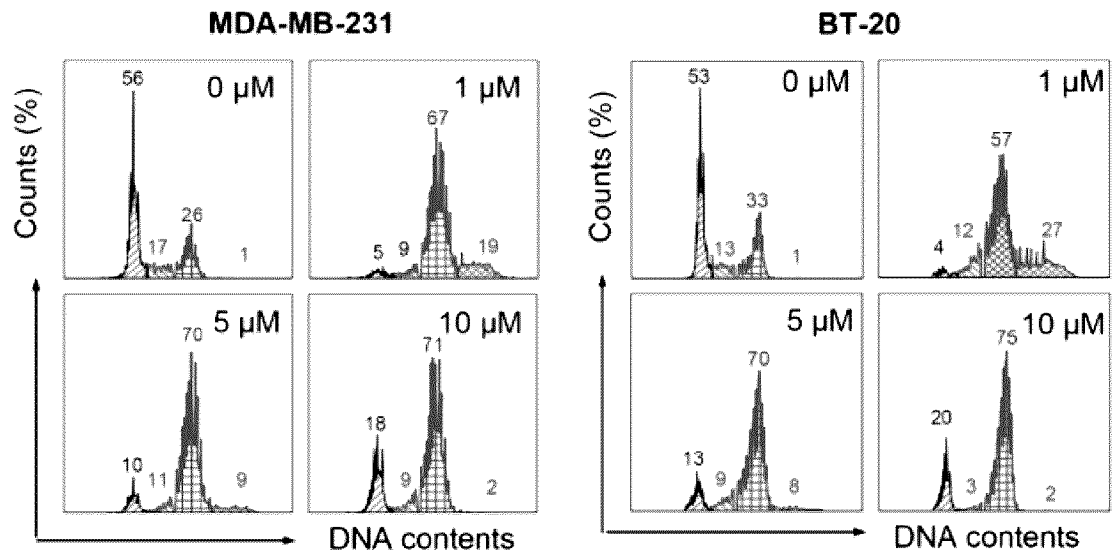
FIG. 6C demonstrates the analysis of the DNA content of MDA-MB-231 and BT-20 cells treated with SLLN-15 or DMSO for 24 hours as analyzed by flow cytometry.
Figure 6D:
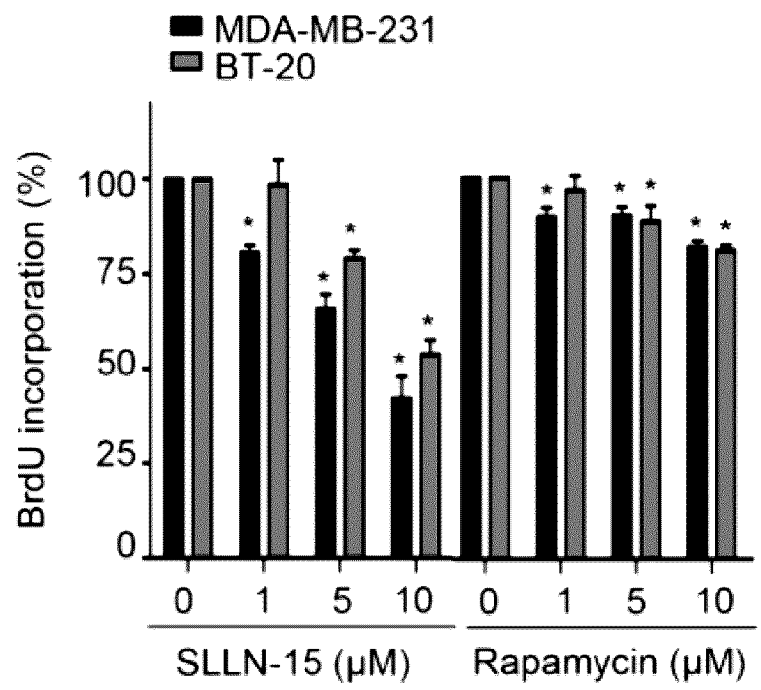
FIG. 6D represents the short-term cell proliferation assay (BrdU incorporation) of MDA-MB-231 and BT-20 cells treated with either DMSO, rapamycin or SLLN-15.

To further determine whether SLLN-15 decreased cell viability by inducing apoptosis or inhibiting cell growth, we used propidium iodide (PI) staining and flow cytometry assays to analyze the DNA contents. As shown in FIG. 6C, SLLN-15 treatment for 24 hours showed no obvious apoptosis (sub-G1 phase), while a significantly higher percentage of cells arrested in G2/M phase and polyploidy (>4N) was observed in SLLN-15 treated MDA-MB-231 and BT-20 cells. In addition, a lower percentage of BrdU-positive cells was observed in SLLN-15-treated cells in a dose-dependent manner (FIG. 6D). Interestingly, compared to the well-known autophagy inducer rapamycin, an mTOR inhibitor that has been tested in various cancer therapies, SLLN-15 was found to be a more potent anti-proliferation agents (FIG. 6D) and autophagy inducer while displaying less mTOR pathway downregulation (FIG. 6E). These results indicate that SLLN-15 displays a profound antitumor effect via inhibition of cell growth in breast cancer cells rather than apoptosis.

SLLN-15 Induces Autophagy by Interfering with the Aurora A/Akt/mTOR Axis

Figure 7A:
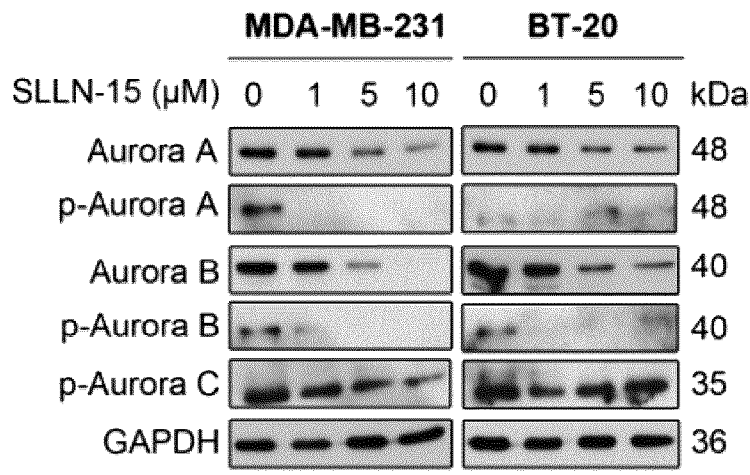
FIG. 7A is a western blot of MDA-MB-231 and BT-20 cells treated with either DMSO or SLLN-15, immunoblotted with antibodies against p-Aurora A/B/C; Aurora A, Aurora B and GAPDH.
Figure 7B:
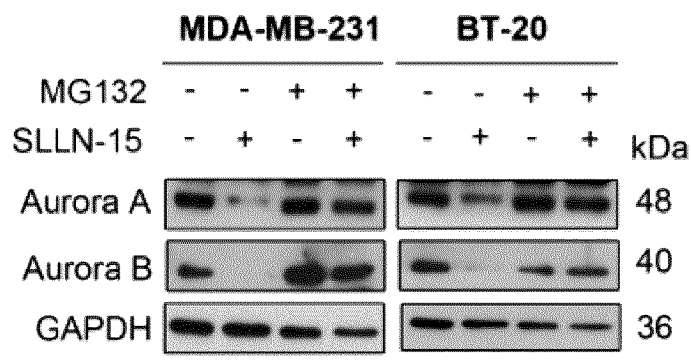
FIG. 7B is a western blot of MDA-MB-231 and BT-20 cells treated with either DMSO or SLLN-15 alone or pre-treated with MG132, immunoblotted with antibodies against Aurora A, Aurora B and GAPDH.

High-throughput screening of SLLN-15 against a panel of select kinases revealed selective inhibition against two kinases, namely Aurora kinase A (91% inhibition) and Janus kinase 2 (JAK2) (85% inhibition), at 100 nM screening concentration (FIG. S3A). To further evaluate cellular Aurora kinase inhibitory activity of SLLN-15, western blot analysis was carried out in both MDA-MB-231 and BT-20 cell lines. As shown in FIG. 7A, SLLN-15 strongly inhibited phosphorylation of both Aurora A at Thr288 and B at Thr232 but not Aurora C at Thr198 at 1 µM. In addition, our data also showed that SLLN-15 treatment decreased both Aurora A and Aurora B expression in a dose-dependent manner (FIG. 7A). To gain further insight into the mechanism underlying the regulation of Aurora A and B by SLLN-15, we next examined whether Aurora A and B were degraded via the proteasome pathway. As shown in FIG. 7B, treatment of MG132, a proteasome inhibitor, could stabilize the protein level of both Aurora A and B in MDA-MB-231 and BT-20 cells, suggesting that the decrease of Aurora A and B observed post SLLN-15 treatment involves the modulation of the proteasome pathway.

Figure 7C:
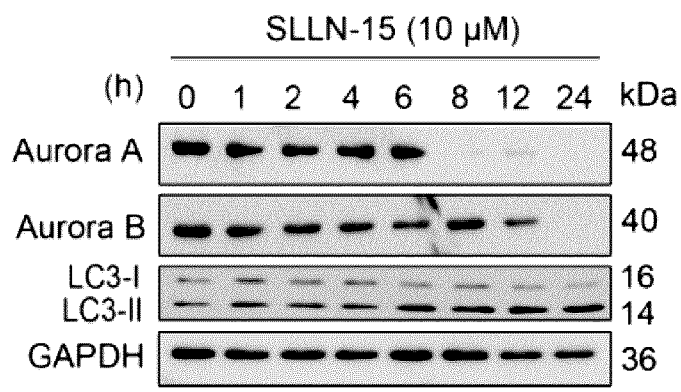
FIG. 7C is a western blot of BT-20 cells treated with either DMSO or SLLN-15 for indicated times, immunoblotted with anti-Aurora A, anti-Aurora B, LC3B and GAPDH antibodies.
Figure 7D:
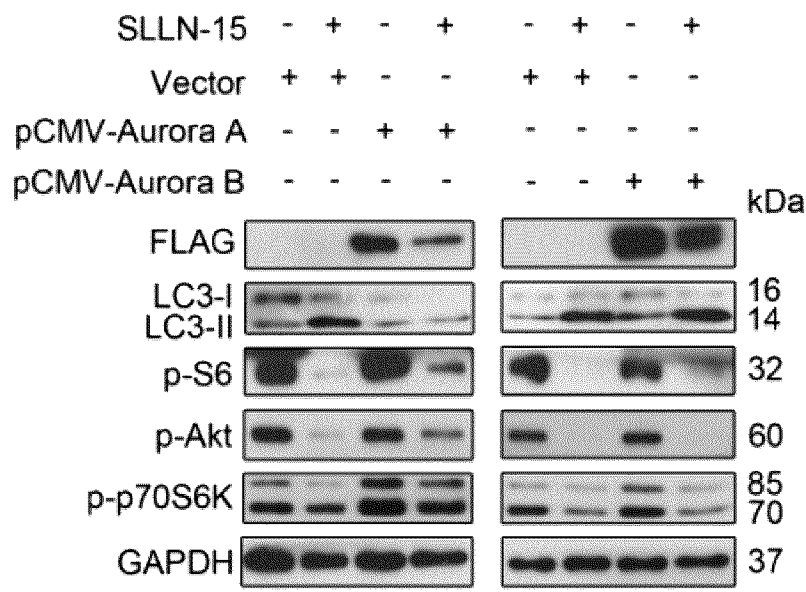
FIG. 7D is western blot of 293T cells transfected with an empty vector (pCMV), pCMV-Aurora A or pCMV-Aurora B plasmids treated with SLLN-15 and immunoblotted with antibodies against FLAG-tag, LC3B, p-S240/244-S6, p-S473-Akt, p-T421/S424-p70S6K and anti-GAPDH.
Figure 7E:
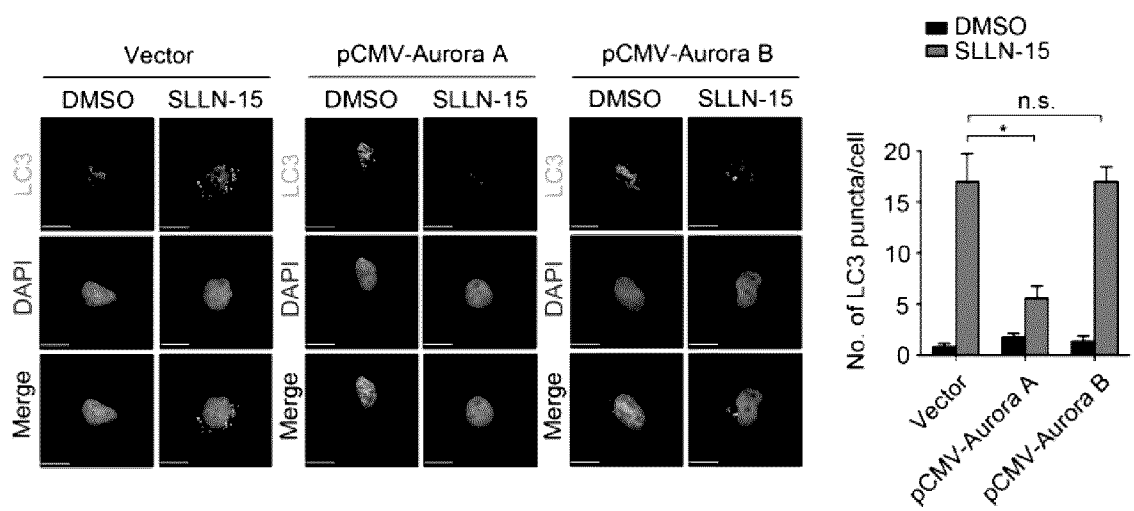
FIG. 7E demonstrates the immunohistochemistry of 293T cells transfected with an empty vector (pCMV), pCMV-Aurora A or pCMV-Aurora B plasmid, treated with either DMSO or SLLN-15 and stained with anti-LC3 antibody (green) and with DAPI (blue).

Since Aurora A inhibition has been reported to activate autophagy via the Akt pathway in cancer cells (Zou Z et al. Aurora kinase A inhibition-induced autophagy triggers drug resistance in breast cancer cells Autophagy 2012; 8:1798-810; Yang H et al. Aurora-A induces cell survival and chemoresistance by activation of Akt through a p53-dependent manner in ovarian cancer cells Int J Cancer 2006; 119:2304-12; Zhang S et al. Aurora-A regulates autophagy through the Akt pathway in human prostate cancer. Cancer Biomark 2017; 19:27-34) and that Aurora B has also been shown to modulate cancer cell invasion via the Akt pathway (Zhou L D et al. RNA interference-mediated knockdown of Aurora-B alters the metastatic behavior of A549 cells via modulation of the phosphoinositide 3-kinase/Akt signaling pathway. Oncol Lett 2014; 8:2063-8; Zhu L B et al. Knockdown of Aurora-B inhibits osteosarcoma cell invasion and migration via modulating PI3K/Akt/NF-kappaB signaling pathway. Int J Clin Exp Pathol 2014; 7:3984-91), we then wanted to determine whether SLLN-15-induced regulation of autophagy was mediated via Aurora A and/or Aurora B. First, our data showed the SLLN-15 downregulated the expression of Aurora A at earlier time points (6 hours post-treatment), which corresponded to the time point of autophagy activation in BT-20 cells (FIG. 7C). Next, to further evaluated the role of Aurora A and Aurora B in SLLN-15-induced autophagy, LC3 lipidation and LC3 puncta were assessed in pCMV-Aurora A or -Aurora B overexpressing BT-20 cells, followed by treatment with SLLN-15 or DMSO. As shown in FIG. 7D, overexpression of Aurora A suppressed the activation of LC3 lipidation and downregulation of Akt/mTOR pathway regulators caused by SLLN-15, but not Aurora B. Consistently, Aurora A overexpression restored SLLN-15 induced accumulation of endogenous LC3 puncta in BT-20 cells (FIG. 7E). Together, our results suggest that the SLLN-15 induced autophagy in breast cancer cells is modulated via the Aurora A/Akt/mTOR.

Figures 8A, 8B:
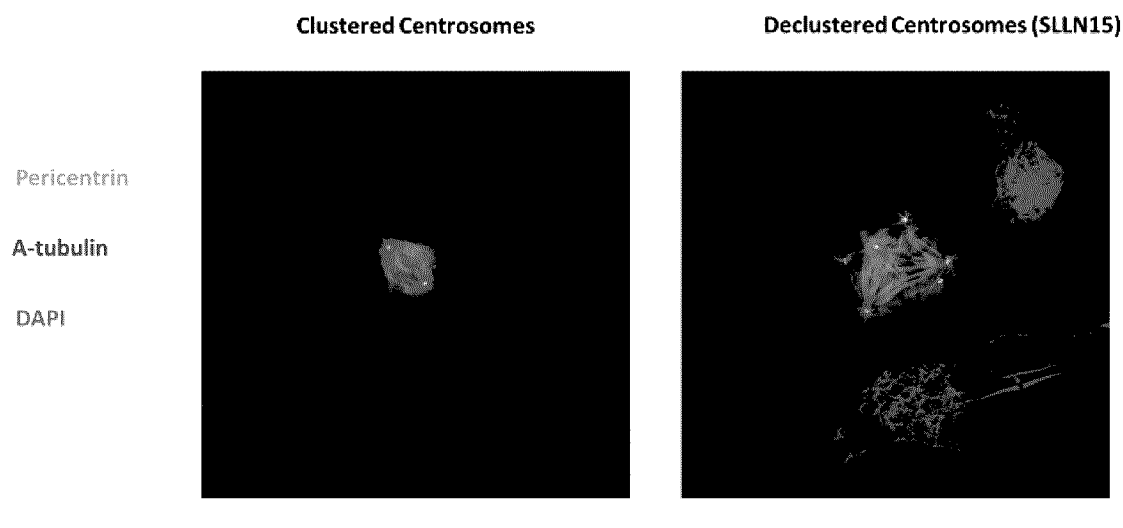
FIG. 8A illustrates clustered centrosomes in untreated cells.
FIG. 8B illustrates declustered centrosomes in SLLN-15-treated cells.

SLLN-15 Shows Selective Anti-Sternness Activity Across Breast Cancer Stem-Like Cells Breast cancer stem-like cells (BCSCs), heterogeneously subsisting as CD24low/CD44high and ALDHhigh subpopulations, are enriched in aggressive breast cancer subtypes and believed to be responsible for driving metastatic colonization. Despite evidence of a clinical association between BCSC and poor prognosis, effective therapeutic means to target this cell population is lacking. We identified SLLN-15 as a compound with selective anti-sternness activity across a panel of cell lines expressing ALDHhigh and CD24low/CD44high markers, including MDA-MB-231, SUM-149PT, BT-20, SKBR3, 4T1 and several anaplastic thyroid cell lines. We identified SLLN-15's main molecular targets as Jak2 and Aurora Kinase A, two kinases that play a role in stem cell signaling and are found to be significantly overexpressed in aggressive triple negative breast cancer, in particular, the claudin-low subtype (n=220). SLLN-15-treated cells exhibited reduced BCSC-marker expression, tumorspheres formation, STAT3 activation and defective mitotic spindle assembly. As evidenced in FIGS. 8A and 8B, SLLN-15 interferes with centrosomes clustering causing inhibition of the cancer cells proliferation. In MDA-MB-231, SLLN-15 also induced loss of cell locomotion concurrent with inhibition of focal adhesion kinase signaling in sorted BCSC subpopulation. In vivo, SLLN-15 was well-tolerated when administered intraperitoneally, and displayed significant anti-metastatic activity in mice bearing MDA-MB-231-M2 or 4T1 tumors. Furthermore, pretreatment with SLLN-15 ex vivo prior to mouse implantation significantly attenuated MDA-MB-231-M2 progression to metastasis. In summary, our data foster that targeting regulatory networks driving sternness represent important therapeutic targets for treating metastatic breast disease.

Discussion

The autophagy pathway has a broad implication in many physiological and pathological processes, including carcinogenesis. Several studies have suggested targeting mediators of autophagy signaling as a promising strategy for cancer drug discovery (Lebovitz C B et al. Precision autophagy: Will the next wave of selective autophagy markers and specific autophagy inhibitors feed clinical pipelines? Autophagy 2015; 11:1949-52; Kenific C M et al. Cellular and metabolic functions for autophagy in cancer cells. Trends Cell Biol 2015; 25:37-45). Although both autophagy upregulation and downregulation have been shown to play roles in carcinogenesis, most studies on therapeutic implications of autophagy have focused on autophagy inhibitors. In general, autophagy is identified as a pro-survival mechanism in cancer cells by removing damaged organelles and recycling the nutrients in response to chemotherapy stress (Fulda S et al. Cell death by autophagy: emerging molecular mechanisms and implications for cancer therapy Oncogene 2015; 34:5105-13). However, a recent finding revealed that autophagy induced by chemotherapeutic agents may have a suppressive role in cancer, revealing two additional functions of autophagy, namely a "cytotoxic function" that results in autophagic cell death; and "cytostatic function" that results in inhibition of cell growth (Gewirtz D A. The four faces of autophagy: implications for cancer therapy Cancer Res 2014; 74:647-51; Liu R et al. Itraconazole suppresses the growth of glioblastoma through induction of autophagy: involvement of abnormal cholesterol trafficking Autophagy 2014; 10:1241-55).

In the present study we describe SLLN-15, a novel small molecule that targets Aurora kinase A, which subsequently leads to trigger autophagy via blockade of the Akt/mTOR pathway. Our work demonstrated that the autophagy induced by SLLN-15 plays a cytostatic role and contributes to inhibit breast cancer cell growth and exerts antitumor activity in preclinical TNBC cell models. SLLN-15 inhibited the growth of breast cancer cells, while no significant apoptosis was observed up to 48 hours post-exposure and this inhibition was rescued while blocking the autophagy pathway, suggesting that short-term exposure to SLLN-15 induced cytostatic autophagy. Conventional anticancer therapies primarily trigger cancer cell death via regulating pathways to induce apoptosis. However, certain cancer types, such as TNBC, can bypass the desired cellular apoptosis, leading to chemoresistance and tumor recurrence. Therefore, apoptosis resistance becomes a tremendous challenge in the development of novel anticancer drugs. As an alternative strategy to inhibit cancer cell growth, cytostatic autophagy has been reported to overcome these limitations by decreasing cancer proliferation independent of the apoptotic pathway. Our results show that SLLN-15 has the capacity to decrease TNBC cell viability while inducing cytostatic autophagy, thereby highlighting SLLN-15 as a promising strategy to overcome these barriers by inhibiting the growth of cancer cells regardless of their sensitivity to apoptosis. Nonetheless, unraveling the complex relationship between autophagy and apoptosis in cell fate determination certainly merits additional consideration to fully understand the crosstalk between these tightly regulated biological processes.

One of the best characterized autophagy-inducing drugs currently being tested as a therapeutic agent in oncology is rapamycin and its analogues. Rapamycin induces autophagy by inhibiting the mTOR/Akt signalling pathway, which is involved in regulating cell proliferation and autophagy activation. Unfortunately, rapamycin's immunosuppressive abilities, independent of autophagy, hinder its use in certain diseases. Side by side comparison of rapamycin and SLLN-15 revealed the superior ability of SLLN-15 to inhibit TNBC proliferation and this with slightly reduced proficiency at inhibiting the mTOR/Akt pathway. Moreover, SLLN-15's ability to co-target JAK2 and downregulate the phosphorylation of its downstream regulator STAT3, a pathway previously demonstrated to be required for the induction of autophagy and cause chemoresistance in brain cancer cells (Pratt J et al. Induction of autophagy biomarker BNIP3 requires a JAK2/STAT3 and MT1-MMP signaling interplay in Concanavalin-A-activated U87 glioblastoma cells Cell Signal 2014; 26:917-24), may support SLLN-15's superiority at activating cytostatic autophagy and inhibiting TNBC proliferation. Recent studies have reported on the efficacy of combining mTOR inhibitors and JAK2 inhibitors, which demonstrated synergistic activity in certain cancer types, including TNBC (Bogani C et al. mTOR inhibitors alone and in combination with JAK2 inhibitors effectively inhibit cells of myeloproliferative neoplasms PLoS One 2013; 8:e54826; Bartalucci N et al. Co-targeting the PI3K/mTOR and JAK2 signalling pathways produces synergistic activity against myeloproliferative neoplasms. J Cell Mol Med 2013; 17:1385-96; Britschgi A et al. JAK2/STAT5 inhibition circumvents resistance to PI3K/mTOR blockade: a rationale for cotargeting these pathways in metastatic breast cancer Cancer Cell 2012; 22:796-811). As such, combination studies investigating the efficacy of SLLN-15 with conventional chemo-agents, similar to current rapamycin/chemo combination trials, where improved drug efficacy and delayed drug resistance is observed (Li J et al. Rapamycin: one drug, many effects. Cell Metab 2014; 19:373-9), merits further examination.

The invention claimed is:

1. A compound of formula

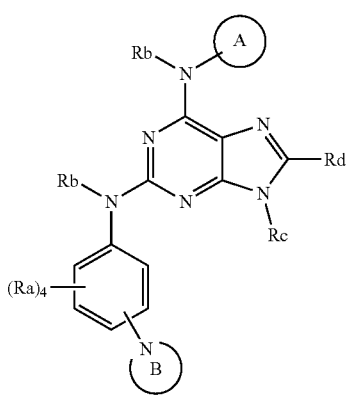

or a pharmaceutically acceptable salt or solvate thereof;
wherein

Ra is independently H, a straight or branched alkyl substituted or not with a halogen, cycloalkyl of 3 to 6 carbon atoms, straight or branched alkoxy substituted or not with a halogen, heteroaryl or halogen, Rb is H or a straight or branched alkyl of 1 to 6 carbon atoms, Rc is H or a straight or branched alkyl of 1 to 6 carbon atoms substituted or not with a halogen, Rd is H, halogen or an alkyl of 1 to 6 carbon atoms, ring A is an optionally substituted saturated 5 to 7 membered cycloalkyl ring attached by a carbon atom of said ring to the nitrogen atom at the C-6 position of the purine core, and said ring A is optionally comprising one or two selenium atoms as ring constituting atoms, and wherein two selenium atoms are adjacent or non-adjacent, or ring A is an optionally substituted 5 to 7 members bridged bicycloalkyl, and ring B is an optionally substituted saturated 5 to 7 membered heterocycloalkyl ring attached by a nitrogen atom of said ring to a carbon atom of the phenylene residue, and wherein said ring optionally comprising one oxygen atom or one or two selenium atoms as ring constituting atoms, and wherein two selenium atoms are adjacent or non-adjacent, provided at least one of ring A and ring B is comprising one or two ring constituting selenium atom.

2. The compound of claim 1, having the formula

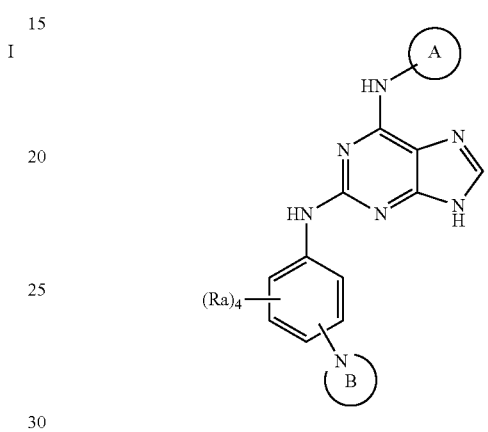

or a pharmaceutically acceptable salt or solvate thereof.

3. The compound of claim 2, wherein Ra is independently H, a straight alkyl or fluoroalkyl of 1-3 carbon atoms; branched alkyl or fluoroalkyl of 3 carbon atoms; straight alkoxy or fluoroalkoxy of 1-3 carbon atoms; branched alkoxy or fluoroalkoxy of 3 carbon atoms, cycloalkyl of 3 carbon atoms, heteroaryl of 5-6 members or fluoride atom.

4. The compound of claim 2, wherein Ra is independently H, methyl, ethyl, n-propyl, isopropyl, n-butyl, sec-butyl, ter-butyl, trifluoromethyl, trifluoromethoxy, methoxy, cyclopropyl, cyclobutyl, cyclopentyl cyclohexyl, heteroaryl of 5-6 members comprising at least one heteroatom selected from oxygen (O), and nitrogen (N); or fluoride atom.

5. The compound of claim 2, wherein ring A is an optionally substituted, saturated 5 to 7 members cycloalkyl or an optionally substituted bicyclo[2,2,1] heptyl or bicyclo[3,1,1] heptyl.

6. The compound of claim 2, wherein ring A is a tetrahydroselenophene, a selenane, a diselenolane or a diselenane.

7. The compound of claim 2, wherein ring A is:

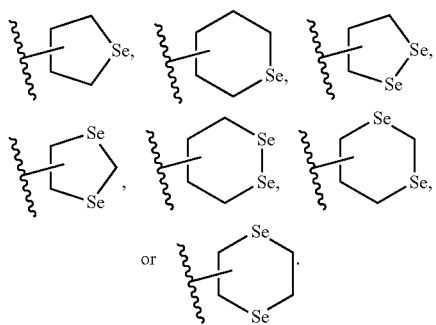

8. The compound of claim 2, wherein ring B is:
an optionally substituted morpholinyl group; an optionally substituted saturated ring attached by a nitrogen atom of said ring to a carbon atom of the phenylene residue, and wherein said ring is comprising 6 members, and is comprising one selenium atom as ring constituting atoms; or
an optionally substituted saturated ring attached by a nitrogen atom of said ring to a carbon atom of the phenylene residue, and wherein said ring is comprising 7 members, and is comprising two selenium atoms as ring constituting atoms, and wherein said selenium atoms are adjacent.

9. The compound of claim 2, wherein ring B is a morpholinyl, a selenomorpholin-4yl of formula

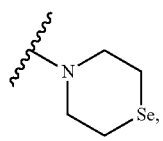

or a 1,2-diselenazepan-5-yl of formula

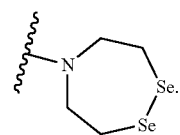

10. The compound of claim 1, wherein each Ra is independently H, a straight alkyl of 1-3 carbon atoms, or branched alkyl of 3 carbon atoms, straight alkoxy of 1-3 carbon atoms or branched alkoxy of 3 carbon atoms, cycloalkyl of 3 carbon atoms, heteroaryl of 5-6 members or fluoride atom; Rb is H or methyl, ethyl, n-propyl, isopropyl; Rc is H or methyl, ethyl, n-propyl, isopropyl or trifluoromethyl; Rd is H, halogen, alkyl of 1 to 6 carbon atoms, and wherein:
ring A is an optionally substituted, saturated 5 to 7 members cycloalkyl or an optionally substituted 5 to 7 members bridged bicycloalkyl and ring B is an optionally substituted saturated ring attached by a nitrogen atom of said ring to a carbon atom of the phenylene residue, and wherein said ring is comprising 5 to 7 members, and is comprising one or two selenium atoms as ring constituting atoms, and wherein two selenium atoms are adjacent or non-adjacent;
ring A is an optionally substituted, saturated ring of 5 to 7 members, comprising one or two ring constituting selenium atom and ring B is an optionally substituted saturated ring attached by a nitrogen atom of said ring to a carbon atom of the phenylene residue, and wherein said ring is comprising 5 to 7 members; or
ring A is an optionally substituted, saturated ring of 5 to 7 members, comprising one or two ring constituting selenium atom and ring B is an optionally substituted saturated ring attached by a nitrogen atom of said ring to a carbon atom of the phenylene residue, and wherein said ring is comprising 5 to 7 members, and is comprising one or two selenium atoms as ring constituting atoms, and wherein two selenium atoms are adjacent or non-adjacent.

11. The compound of claim 1, wherein each Ra is H; Rb is H; Rc is H; Rd is H, ring A is an optionally substituted, saturated 5 to 7 members cycloalkyl or an optionally substituted 5 to 7 members bridged bicycloalkyl and ring B is an optionally substituted saturated ring attached by a nitrogen atom of said ring to a carbon atom of the phenylene residue, and wherein said ring is comprising 5 to 7 members, and is comprising one or two selenium atoms as ring constituting atoms, and wherein two selenium atoms are adjacent or non-adjacent.

12. The compound of claim 1, wherein each Ra is H; Rb is H; Rc is H; Rd is H, ring A is an optionally substituted, saturated ring of 5 to 7 members, comprising one or two ring constituting selenium atom and ring B is an optionally substituted saturated ring attached by a nitrogen atom of said ring to a carbon atom of the phenylene residue, and wherein said ring is comprising 5 to 7 members.

13. The compound of claim 1, wherein each Ra is H; Rb is H; Rc is H; Rd is H, ring A is an optionally substituted, saturated ring of 5 to 7 members, comprising one or two ring constituting selenium atom and ring B is an optionally substituted saturated ring attached by a nitrogen atom of said ring to a carbon atom of the phenylene residue, and wherein said ring is comprising 5 to 7 members, and is comprising one or two selenium atoms as ring constituting atoms, and wherein two selenium atoms are adjacent or non-adjacent.

14. The compound of claim 1, wherein said compound is:

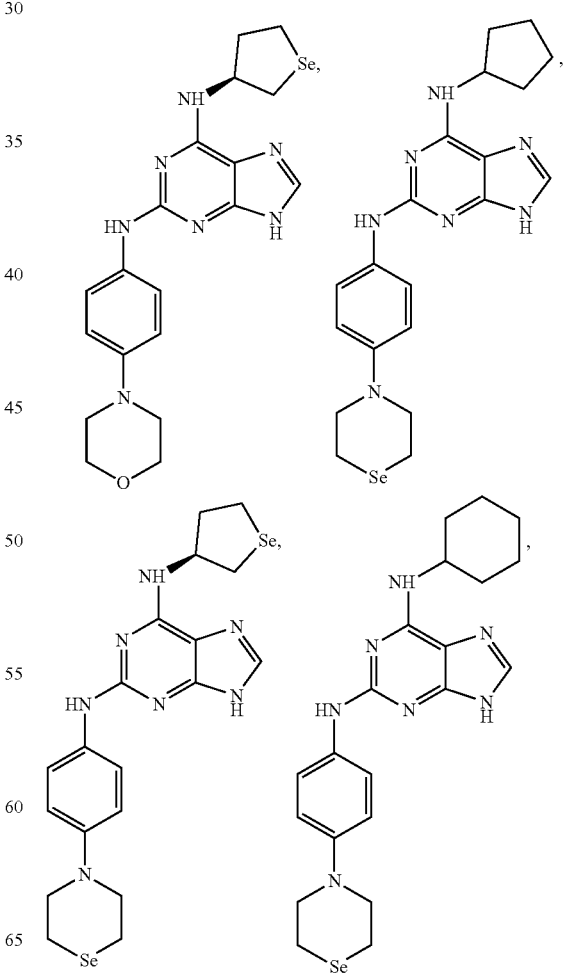

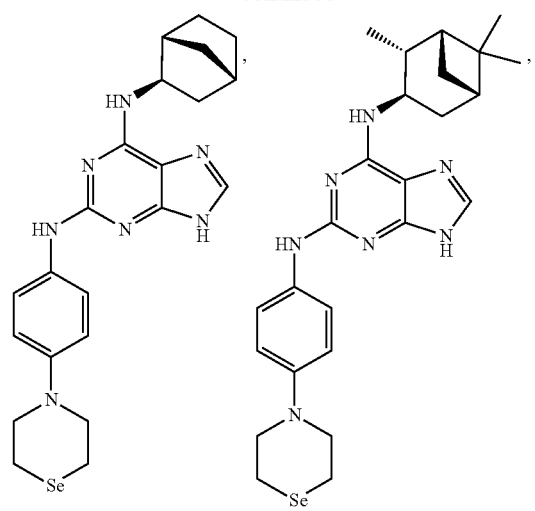

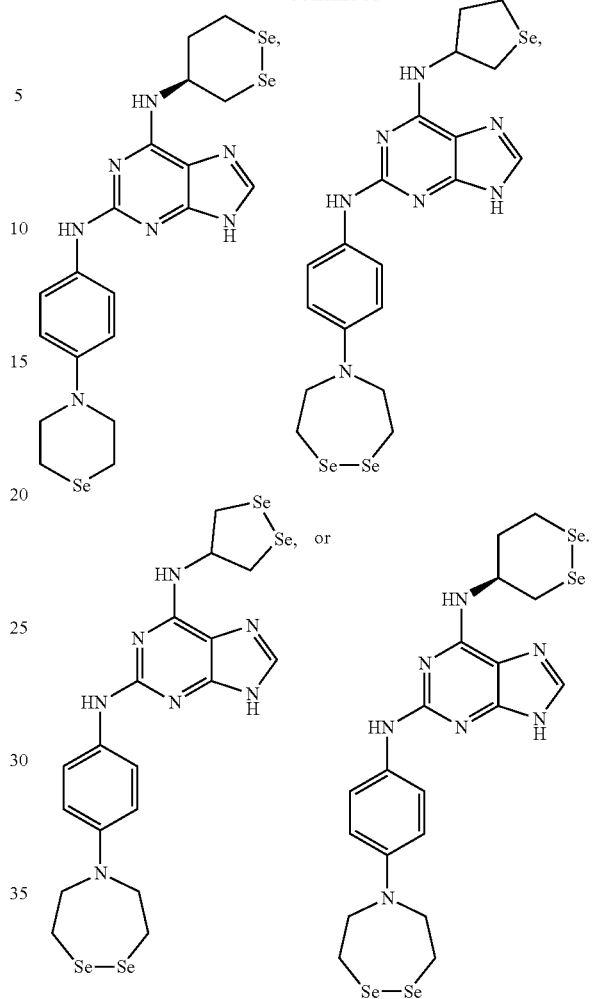

15. A pharmaceutical composition comprising a compound as defined in claim 2, or a pharmaceutically acceptable salt or solvate thereof, and one or more pharmaceutically acceptable carrier and/or excipient.

16. The pharmaceutical composition of claim 15, further comprising a therapeutically effective amount of at least one or more therapeutic agents selected from the group consisting of alkylating agents, anti-metabolites, plant alkaloids, terpenoids, vinca alkaloids, podophyllotoxin, taxanes, topoisomerase inhibitors, and cytotoxic antibiotics.

17. A method for treating cancer comprising administering to a patient in need thereof a therapeutically effective amount of the compound of claim 2.

18. The method of claim 17, comprising administering to a patient in need thereof a therapeutically effective amount of at least one or more therapeutic agents selected from the group consisting of alkylating agents, anti-metabolites, plant alkaloids, terpenoids, vinca alkaloids, podophyllotoxin, taxanes, topoisomerase inhibitors, and cytotoxic antibiotics.

19. The method of claim 17 comprising co-modulating and/or co-inhibiting the function of Aurora A and Jak2 kinases.

20. The method of claim 17 comprising reducing metastasis of metastatic cells of said cancer in said patient in need thereof.

* * * * *

SEQUENCE LISTING

<160> NUMBER OF SEQ ID NOS: 12

<210> SEQ ID NO 1
<211> LENGTH: 29
<212> TYPE: DNA
<213> ORGANISM: Artificial Sequence

```
<220> FEATURE:
<223> OTHER INFORMATION: Sense primer sequence for Aurora A

<400> SEQUENCE: 1
cgggatccat ggaccgatct aaagaaaac                                               29

<210> SEQ ID NO 2
<211> LENGTH: 30
<212> TYPE: DNA
<213> ORGANISM: Artificial Sequence
<220> FEATURE:
<223> OTHER INFORMATION: Antisense primer sequence for Aurora A

<400> SEQUENCE: 2
ccgctcgaga gactgtttgc tagctgattc                                              30

<210> SEQ ID NO 3
<211> LENGTH: 27
<212> TYPE: DNA
<213> ORGANISM: Artificial Sequence
<220> FEATURE:
<223> OTHER INFORMATION: Sense primer sequence for Aurora B

<400> SEQUENCE: 3
cgggatccat gagccgctcc aatgtcc                                                 27

<210> SEQ ID NO 4
<211> LENGTH: 27
<212> TYPE: DNA
<213> ORGANISM: Artificial Sequence
<220> FEATURE:
<223> OTHER INFORMATION: Antisense primer sequence for Aurora B

<400> SEQUENCE: 4
ccgctcgagg gcgacagatt gaagggc                                                 27

<210> SEQ ID NO 5
<211> LENGTH: 21
<212> TYPE: RNA
<213> ORGANISM: Artificial Sequence
<220> FEATURE:
<223> OTHER INFORMATION: non-targeted siRNA sense sequence
<220> FEATURE:
<221> NAME/KEY: modified_base
<222> LOCATION: (20)...(21)
<223> OTHER INFORMATION: deoxythymidine

<400> SEQUENCE: 5
uucuccgaac gugucacgun n                                                       21

<210> SEQ ID NO 6
<211> LENGTH: 22
<212> TYPE: RNA
<213> ORGANISM: Artificial Sequence
<220> FEATURE:
<223> OTHER INFORMATION: non-targeted siRNA antisense sequence
<220> FEATURE:
<221> NAME/KEY: modified_base
<222> LOCATION: (21)...(22)
<223> OTHER INFORMATION: deoxythymidine

<400> SEQUENCE: 6
acggugacac guucggagaa nn                                                      22

<210> SEQ ID NO 7
<211> LENGTH: 24
<212> TYPE: RNA
```

```
<213> ORGANISM: Artificial Sequence
<220> FEATURE:
<223> OTHER INFORMATION: Beclin1 siRNA sense sequence
<220> FEATURE:
<221> NAME/KEY: modified_base
<222> LOCATION: (23)...(24)
<223> OTHER INFORMATION: deoxythymidine

<400> SEQUENCE: 7
cucaaguuca ugcugacgaa uunn                                              24

<210> SEQ ID NO 8
<211> LENGTH: 24
<212> TYPE: RNA
<213> ORGANISM: Artificial Sequence
<220> FEATURE:
<223> OTHER INFORMATION: Beclin1 siRNA antisense sequence
<220> FEATURE:
<221> NAME/KEY: modified_base
<222> LOCATION: (23)...(24)
<223> OTHER INFORMATION: deoxythymidine

<400> SEQUENCE: 8
uucgucagca ugaacuugag uunn                                              24

<210> SEQ ID NO 9
<211> LENGTH: 24
<212> TYPE: RNA
<213> ORGANISM: Artificial Sequence
<220> FEATURE:
<223> OTHER INFORMATION: Atg5 siRNA sense sequence
<220> FEATURE:
<221> NAME/KEY: modified_base
<222> LOCATION: (23)...(24)
<223> OTHER INFORMATION: deoxythymidine

<400> SEQUENCE: 9
agauugaagg aucaacuauu uunn                                              24

<210> SEQ ID NO 10
<211> LENGTH: 24
<212> TYPE: RNA
<213> ORGANISM: Artificial Sequence
<220> FEATURE:
<223> OTHER INFORMATION: Atg5 siRNA antisense sequence
<220> FEATURE:
<221> NAME/KEY: modified_base
<222> LOCATION: (23)...(24)
<223> OTHER INFORMATION: deoxythymidine

<400> SEQUENCE: 10
aauaguugau ccuucaaucu uunn                                              24

<210> SEQ ID NO 11
<211> LENGTH: 24
<212> TYPE: RNA
<213> ORGANISM: Artificial Sequence
<220> FEATURE:
<223> OTHER INFORMATION: Atg7 siRNA sense sequence
<220> FEATURE:
<221> NAME/KEY: modified_base
<222> LOCATION: (23)...(24)
<223> OTHER INFORMATION: deoxythymidine

<400> SEQUENCE: 11
gccugcugag gagcucucca uunn                                              24

<210> SEQ ID NO 12
<211> LENGTH: 22
```

```
<212> TYPE: RNA
<213> ORGANISM: Artificial Sequence
<220> FEATURE:
<223> OTHER INFORMATION: Atg7 siRNA antisense sequence

<400> SEQUENCE: 12
uggagagcuc cucagcaggc uu                                            22
```